(12) United States Patent
Frantz

(10) Patent No.: US 11,364,189 B2
(45) Date of Patent: *Jun. 21, 2022

(54) METHOD FOR THE TREATMENT OF KERATIN MATERIALS USING AMIDE C-GLYCOSIDE DERIVATIVES, AND COSMETIC COMPOSITION CONTAINING SAME

(71) Applicant: L'OREAL, Paris (FR)

(72) Inventor: Marie-céline Frantz, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/347,336

(22) PCT Filed: Nov. 7, 2017

(86) PCT No.: PCT/EP2017/078480
§ 371 (c)(1),
(2) Date: May 3, 2019

(87) PCT Pub. No.: WO2018/083341
PCT Pub. Date: May 11, 2018

(65) Prior Publication Data
US 2019/0274940 A1  Sep. 12, 2019

(30) Foreign Application Priority Data

Nov. 7, 2016 (FR) ...................................... 1660743
Nov. 6, 2017 (FR) ...................................... 1760398

(51) Int. Cl.
| | | |
|---|---|---|
| *A61K 8/60* | (2006.01) | |
| *A61Q 19/02* | (2006.01) | |
| *A61Q 19/08* | (2006.01) | |
| *A61Q 5/08* | (2006.01) | |
| *C07H 1/00* | (2006.01) | |
| *C07H 3/02* | (2006.01) | |
| *C07H 17/08* | (2006.01) | |
| *C07D 493/04* | (2006.01) | |
| *C07D 405/06* | (2006.01) | |
| *C07D 309/10* | (2006.01) | |

(52) U.S. Cl.
CPC ................ *A61K 8/602* (2013.01); *A61K 8/60* (2013.01); *A61Q 5/08* (2013.01); *A61Q 19/02* (2013.01); *A61Q 19/08* (2013.01); *C07D 309/10* (2013.01); *C07D 405/06* (2013.01); *C07D 493/04* (2013.01); *C07H 1/00* (2013.01); *C07H 3/02* (2013.01); *C07H 17/08* (2013.01)

(58) Field of Classification Search
CPC ...................................................... A61Q 19/02
See application file for complete search history.

(56) References Cited

U.S. PATENT DOCUMENTS

| | | | |
|---|---|---|---|
| 7,862,804 B2* | 1/2011 | Rolland ................. | A61K 8/602 424/62 |
| 2005/0002889 A1 | 1/2005 | Dalko et al. | |
| 2007/0265210 A1 | 11/2007 | Breton | |
| 2009/0325890 A1 | 12/2009 | Breton | |

FOREIGN PATENT DOCUMENTS

| | | |
|---|---|---|
| EP | 1 589 010 A1 | 10/2005 |
| EP | 1 844 757 A1 | 10/2007 |
| FR | 2 899 468 A1 | 10/2007 |
| WO | WO-2004091557 A2 * 10/2004 | ............. C11D 3/227 |
| WO | WO 2016/177908 A2 | 11/2016 |

OTHER PUBLICATIONS

Ide et al., "Studies on D-Glucuronamide and related compounds. VIII. Synthesis of D-glucuronic acid arylamides", Journal of the Pharmaceutical Society of Japan, vol. 85, No. 3, pp. 220-226, Jan. 1965. XP009193104.
Haworth et al., "21. The properties of 3: 6-anhydroglucose", Journal of the Chemical Society, pp. 88-102, Jan. 1941. XP055336156.

* cited by examiner

*Primary Examiner* — Gina C Justice
(74) *Attorney, Agent, or Firm* — Polsinelli PC

(57) ABSTRACT

The present invention relates to a method for the cosmetic treatment of keratin materials, comprising the application of a composition to the keratin materials, such as the skin, said composition comprising a compound (I), wherein R1, R2 and R3 are as defined in the description and S* is a mono or polysaccharide.

10 Claims, No Drawings

METHOD FOR THE TREATMENT OF KERATIN MATERIALS USING AMIDE C-GLYCOSIDE DERIVATIVES, AND COSMETIC COMPOSITION CONTAINING SAME

CROSS REFERENCE TO RELATED APPLICATIONS

This application is a National Phase filing under 35 U.S.C. § 371 of PCT/EP2017/078480 filed on Nov. 7, 2017; and this application claims priority to Application No. 1660743 filed in France on Nov. 7, 2016, and Application No. 1760398 filed in France on Nov. 6, 2017. The entire contents of each application are hereby incorporated by reference.

The invention relates to novel C-glycoside compounds comprising an amide group, to a cosmetic composition comprising same, to a preparation process, to the use of said C-glycosides for treating keratin materials and in particular the skin, and to a process for treating keratin materials using said C-glycosides.

In particular, the present invention relates to the cosmetic use of C-glycoside amide derivative compounds, in particular the use thereof for depigmenting and/or bleaching keratin materials and in particular the skin, and of novel derivatives, and to compositions, especially cosmetic compositions, containing same.

At various periods in their life, some people develop darker and/or more coloured spots on the skin and more especially on the hands and the face, giving the skin heterogeneity. These spots are due especially to a high concentration of melanin in the keratinocytes located at the surface of the skin.

The use of harmless topical depigmenting substances with good efficacy is most particularly sought in order to treat pigmentation spots.

The mechanism of formation of skin pigmentation, i.e. the mechanism of formation of melanin, is particularly complex and schematically involves the following main steps: Tyrosine→Dopa→Dopaquinone→Dopachrome→Melanin Tyrosinase (monophenol dihydroxyl phenylalanine: oxygen oxidoreductase EC 1.14.18.1) is the essential enzyme operating in this sequence of reactions. It especially catalyses the reaction for the transformation of tyrosine into dopa (dihydroxyphenylalanine) by virtue of its hydroxylase activity and the reaction for the transformation of dopa into dopaquinone by virtue of its oxidase activity. This tyrosinase acts only when it is in mature form under the action of certain biological factors.

A substance is acknowledged as being depigmenting if it acts directly on the vitality of the epidermal melanocytes where melanogenesis takes place, and/or if it interferes with one of the steps in melanin biosynthesis, either by inhibiting one of the enzymes involved in melanogenesis, or by intervening as a structural analogue of one of the chemical compounds of the melanin synthesis chain, which chain can then be blocked and thus bring about depigmentation.

Arbutin and kojic acid are known as skin depigmenting agents. Substances which have an efficient depigmenting action have been sought.

The need nevertheless remains for a novel agent for bleaching keratin materials and in particular human skin, which is stable in a composition, readily formulable in particular in aqueous formulations, or alternatively which has reinforced action so as to be able to be used in a smaller amount, which considerably reduces the side effects that may be observed.

In this regard, the Applicant has, surprisingly and unexpectedly, discovered that C-glycoside amide derivatives have good depigmenting activity, even at low concentration, without showing any cytotoxicity.

Women, and men, currently have, furthermore, a tendency to wish to appear youthful for as long as possible and consequently seek to tone down the signs of ageing on the skin, which are reflected in particular by wrinkles and fine lines, thinning of the epidermis and/or a flaccid and withered skin appearance. In this regard, the advertising and fashion industries mention products for retaining radiant and wrinkle-free skin, signs of youthful skin, for as long as possible, all the more so since physical appearance has an effect on the psyche and/or on morale.

The skin is constituted of two compartments, a surface compartment, the epidermis, and the other deeper compartment, the dermis, which interact. Natural human epidermis is composed mainly of three types of cells, namely keratinocytes, which form the vast majority, melanocytes and Langerhans cells. Each of these types of cells contributes, by virtue of its intrinsic functions, to the essential role played in the body by the skin, in particular the role of protecting the body against external attacking factors, which is known as the "barrier function".

The epidermis is conventionally divided into a basal layer of keratinocytes that constitutes the germinative layer of the epidermis, a spinous layer constituted of several layers of polyhedral cells positioned on the germinative layers, one to three "granular" layers constituted of flattened cells containing distinct cytoplasmic inclusions, keratohyalin granules, and finally the cornified layer (or stratum corneum), constituted of a set of layers of keratinocytes at the terminal stage of their differentiation, known as corneocytes. Corneocytes are anuclear cells mainly constituted of a fibrous material containing cytokeratins, surrounded by a cornified envelope.

The dermis provides the epidermis with a solid support. It is also its nourishing element. It is constituted mainly of fibroblasts and an extracellular matrix composed predominantly of collagen, elastin and a substance known as ground substance. These components are synthesized by the fibroblasts. Leukocytes, mast cells or else tissue macrophages are also found therein. Finally, blood vessels and nerve fibres pass through the dermis. The cohesion between the epidermis and the dermis is provided by the dermo-epidermal junction.

The epidermis is constantly engaged in producing new keratinocytes to compensate for the continuous loss of epidermal cells at the cornified layer. However, in the course of ageing, a decrease in the number of cells in the proliferation phase, and consequently a decrease of the live epidermal layers, may be observed physiologically. By limiting and/or delaying the passing of cells into the differentiation phase, the pool of young cells is maintained.

It is thus important to preserve this pool of proliferative cells, by preventing or delaying their differentiation, in order to contribute towards delaying the onset of the signs of ageing.

During chronological and/or actinic ageing, the dermis and the epidermis undergo numerous modifications and degradations which are reflected, with age, by flaccidness and a loss of suppleness of the skin.

Among the components degraded (in particular collagen and elastin), proteoglycans (also referred to as PGs) and glycosaminoglycans (also referred to as GAGs) are also adversely affected. Specifically, over the course of ageing, the fibroblasts and keratinocytes produce fewer and fewer PGs and GAGs and the synthesis thereof is imperfect. This results in significant disorganization: the deposition of GAGs on the protein backbone forming the PG is abnormal, which results in a decrease in the tonicity of the tissues and thus a loss of suppleness of the skin, and also in particular a lower avidity of these PGs for water and therefore a reduction in moisturization of the tissues. Restoring a normal production of PGs and GAGs by fibroblasts and keratinocytes contributes partially toward compensating for the loss of moisturization of the skin.

Moreover, with age, a decrease in the expression of proteins playing a key role in the maintenance of the barrier function of the skin, such as filaggrin and membrane transglutaminase, is particularly observed.

The importance of combating the degradation of the various structural proteins of tissues is therefore understood on reading the aforementioned, and possible routes of action for preventing or limiting the consequences of skin ageing are in particular the stimulation of the synthesis of structural molecules of the skin, such as collagen, and in particular collagen III, and also filaggrin, laminin-5, FADS2 (fatty acid desaturase 2) and/or membrane transglutaminase.

The applicant has also demonstrated, surprisingly, that some C-glycoside compounds comprising an amide group of formula (I) and in particular the compounds (Ia$^1$), (Ia$^2$), (IBB), (Ib$^1$), (Ib$^2$) and/or (Ic) and even more particularly the compounds 1 to 21 described below have anti-ageing and/or moisturizing properties.

A first subject of the invention is a process for the cosmetic treatment of keratin materials, especially the skin, using at least one compound of formula (I) as defined below or a cosmetic composition containing at least one compound of formula (I).

The invention relates to the non-therapeutic cosmetic use of at least one compound of formula (I) as defined below, especially of at least one compound of formula (Ia$^1$), (Ia$^2$), (IBB), (Ib$^1$), (Ib$^2$) and/or (Ic) and even more particularly of at least one compound 1 to 21 defined below, as an agent for bleaching, lightening and/or depigmenting keratin materials, especially the skin.

A subject of the invention is also a non-therapeutic cosmetic treatment process for depigmenting, lightening and/or bleaching keratin materials, especially the skin, comprising the application to the skin of at least one compound of formula (I), especially of at least one compound of formula (Ia$^1$), (Ia$^2$), (IBB), (Ib$^1$), (Ib$^2$) and/or (Ic) and even more particularly of at least one compound 1 to 21 as defined below or of a composition containing same.

A subject of the invention is also the dermatological use of at least one compound of formula (I) as defined below, especially of at least one compound of formula (Ia$^1$), (Ia$^2$), (IBB), (Ib$^1$), (Ib$^2$) and/or (Ic) and even more particularly of at least one compound 1 to 21, for depigmenting, lightening and/or bleaching the skin.

The compounds of formula (I) in accordance with the invention, as defined below, especially the compounds of formula (Ia$^1$), (Ia$^2$), (IBB), (Ib$^1$), (Ib$^2$) and/or (Ic) and even more particularly the compounds 1 to 21, make it possible to depigment and/or lighten efficiently, or even bleach, keratin materials, especially human skin. They are especially intended to be applied to the skin of individuals who have brownish pigmentation spots, liver spots, or to the skin of individuals who wish to combat the appearance of a brownish colour originating from melanogenesis.

For the purposes of the present invention, the term "keratin materials" means human keratin materials, and in particular human skin, bodily hairs, eyelashes, head hair, lips and nails.

The compounds of formula (I) in accordance with the invention may also make it possible to depigment and/or lighten bodily hairs, eyelashes, head hair, and also lips and/or nails.

More particularly, the term "keratin materials" denotes human skin.

A subject of the invention is also the novel compounds of formula (Ia$^1$), (Ia$^2$), (IBB), (Ib$^1$), (Ib$^2$) and/or (Ic) as defined below.

Similarly, a subject of the invention is a cosmetic composition comprising, in a physiologically acceptable medium, at least one compound of formula (I) as defined below, in particular at least one compound of formula (Ia$^1$), (Ia$^2$), (IBB), (Ib$^1$), (Ib$^2$) and/or (Ic) and even more particularly at least one compound chosen from the compounds 1 to 21 defined below.

In addition, a subject of the present invention is thus also the cosmetic use of a C-glycoside compound of formula (I) as defined below and in particular the compounds (Ia$^1$), (Ia$^2$), (IBB), (Ib$^1$), (Ib$^2$) and/or (Ic) and even more particularly the compounds 1 to 21 described below, as an anti-ageing agent and/or moisturizing agent.

The compounds (I), and in particular the compounds (Ia$^1$), (Ia$^2$), (IBB), (Ib$^1$), (Ib$^2$) and/or (Ic) and even more particularly the compounds 1 to 21 described below make it possible to treat keratin materials and in particular the skin, in particular for reducing and/or delaying the signs of ageing of the skin and/or skin integuments, and/or for maintaining and/or stimulating the moisturization of the skin and skin integuments.

The invention also relates to a process for cosmetic treatment of keratin materials, in particular the skin, comprising the application, to said materials, of a cosmetic composition comprising at least one compound of formula (I), or in particular at least one compound (Ia$^1$), (Ia$^2$), (IBB), (Ib$^1$), (Ib$^2$) and/or (Ic) or even more particularly at least one compound of structure 1 to 21 described below.

According to another particular embodiment of the invention, the composition is intended for topical administration to keratin materials such as the skin.

The compounds (I), in particular the compounds (Ia$^1$), (Ia$^2$), (IBB), (Ib$^1$), (Ib$^2$) and/or (Ic) and more particularly the compounds 1 to 21 described below, make it possible in particular to prevent and/or treat the signs of skin ageing.

Among the signs of skin ageing, mention is in particular made of a loss of firmness and/or elasticity and/or tonicity and/or suppleness of the skin, the formation of wrinkles and fine lines, expression lines, in particular on the forehead and in the space between the eyebrows, perioral wrinkles and fine lines, and/or slackening in the area around the lips, in particular in the top lip area (area between the top lip and the nose), a dull appearance of the complexion, and the papery appearance of the skin.

The compounds (I), and in particular the compounds (Ia$^1$), (Ia$^2$), (IBB), (Ib$^1$), (Ib$^2$) and/or (Ic) and more particularly the compounds 1 to 21 described below, make it possible to prevent and/or treat the signs of skin ageing, in particular the loss of firmness and/or of elasticity and/or of tonicity and/or of suppleness of the skin.

The compounds (I), and in particular the compounds (Ia$^1$), (Ia$^2$), (IBB), (Ib$^1$), (Ib$^2$) and/or (Ic) and more particularly the compounds 1 to 21 described below, also make it possible to prevent and/or treat wrinkles and fine lines, in particular of the face and/or of the body, most particularly of the face and/or of the neck.

The compounds (I), and in particular the compounds (Ia¹), (Ia²), (IBB), (Ib¹), (Ib²) and/or (Ic) and more particularly the compounds 1 to 21 described below, also make it possible to maintain and/or stimulate the moisturization and/or combat the drying out of keratin materials such as the skin.

Compounds of Formula (I)

A subject of the invention is the non-therapeutic cosmetic use of at least one compound of formula (I) as an agent for bleaching, lightening and/or depigmenting keratin materials, especially the skin, said compounds corresponding to formula (I) below:

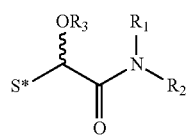
(I)

and also the solvates thereof such as hydrates, the optical and geometric isomers and tautomers thereof and the organic or mineral base or acid salts thereof, in which formula (I):

S* denotes a monosaccharide sugar radical or denotes a polysaccharide sugar radical comprising from 2 to 5 saccharide units, preferably from 2 to 3 saccharide units, preferentially S* denotes a sugar radical comprising 1 or 2 saccharide unit(s) (monosaccharide or disaccharide), each saccharide unit (the saccharide unit in the case of a monosaccharide or each saccharide unit in the case of polysaccharides) comprising one or more hydroxyl groups optionally substituted with a radical R' chosen from:
  i) $(C_1-C_6)$alkyl; or
  ii) $(C_2-C_6)$alkenyl; or
  iii) an acetyl radical; or
  iv) a protective group (PG) for hydroxyl function(s), such as $(C_2-C_6)$alkyl(thio)carbonyl or benzyl;
said monosaccharide or polysaccharide radical possibly also comprising one or more amino groups $NR_bR_c$ with $R_b$ and $R_c$, which may be identical or different, representing a hydrogen atom, an acetyl group, or a protective group for the amino function, such as $(C_2-C_6)$alkyl(thio)carbonyl;
said monosaccharide or polysaccharide radical being connected to the rest of the molecule by a bond between the $C_1$ carbon atom of one of the sugars of said monosaccharide or polysaccharide radical, this bond possibly being α or β anomeric;

$R_3$ represents
  i) a hydrogen atom; or
  ii) a $(C_1-C_{18})$alkyl group; or
  iii) a $(C_2-C_{18})$alkenyl group; or
  iv) a hydroxyl-function-protective group (PG) such as $(C_1-C_{18})$alkyl(thio)carbonyl, such as an acetyl group, $(C_2-C_{18})$alkenyl(thio)carbonyl or an aryl$(C_1-C_4)$alkyl radical optionally substituted in particular with at least one hydroxyl and/or saturated or unsaturated $(C_1-C_4)$alkoxy group;

$R_1$ represents:
  i) a hydrogen atom; or
  ii) a $(C_1-C_{18})$alkyl group; or
  iii) a $(C_2-C_{18})$alkenyl group;

$R_2$ represents:
  i) an optionally substituted aryl or heteroaryl radical; or
  (ii) a radical of formula (B1):

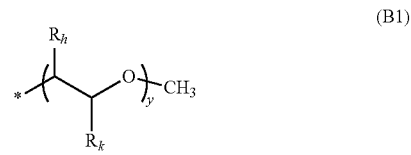
(B1)

in which:
  $R_h$ and $R_k$, independently of one another, denote a hydrogen atom or a methyl radical, it being understood that $R_h$ and $R_k$ cannot simultaneously denote a methyl radical;
  y=1 to 10, limits included;
iii) a radical of formula (B2):

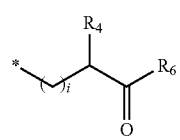
(B2)

in which:
  i=0 or 1;
  $R_4$ represents
    i) a hydrogen atom, or
    ii) a radical chosen from the radicals (a1) to (a32) described below:

(a1)

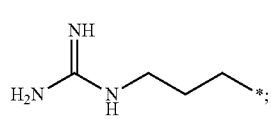
(a2)

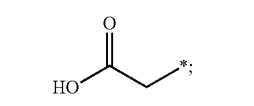
(a3)

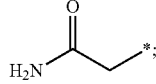
(a4)

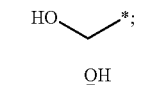
(a5)

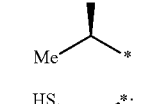
(a6)

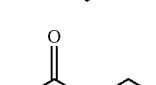
(a7)

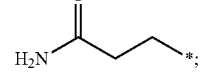
(a8)

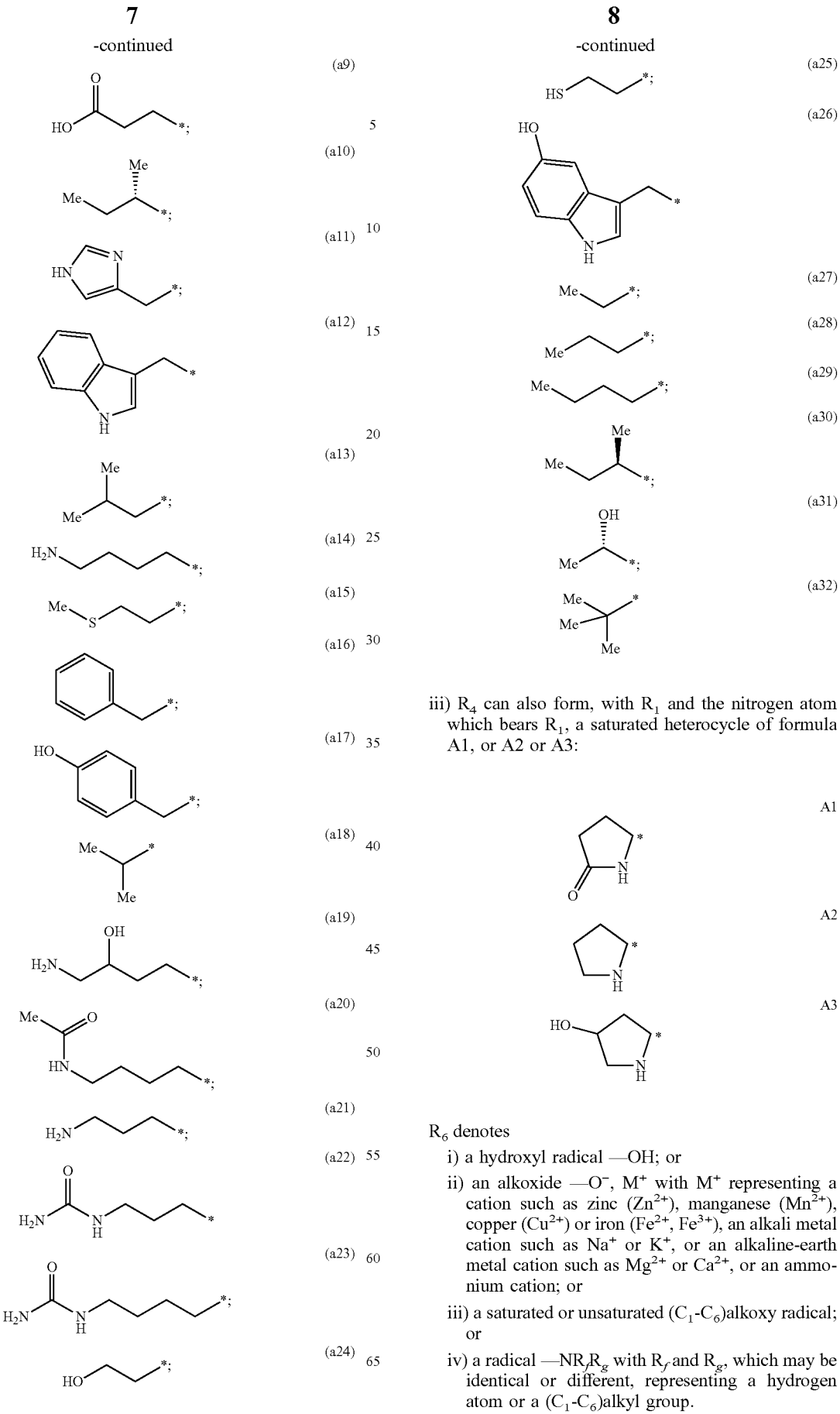

iii) $R_4$ can also form, with $R_1$ and the nitrogen atom which bears $R_1$, a saturated heterocycle of formula A1, or A2 or A3:

$R_6$ denotes
  i) a hydroxyl radical —OH; or
  ii) an alkoxide —O⁻, M⁺ with M⁺ representing a cation such as zinc ($Zn^{2+}$), manganese ($Mn^{2+}$), copper ($Cu^{2+}$) or iron ($Fe^{2+}$, $Fe^{3+}$), an alkali metal cation such as $Na^+$ or $K^+$, or an alkaline-earth metal cation such as $Mg^{2+}$ or $Ca^{2+}$, or an ammonium cation; or
  iii) a saturated or unsaturated ($C_1$-$C_6$)alkoxy radical; or
  iv) a radical —$NR_fR_g$ with $R_f$ and $R_g$, which may be identical or different, representing a hydrogen atom or a ($C_1$-$C_6$)alkyl group.

In the context of the present invention, the asterisk "*" denotes the point of attachment of the radical to the rest of the compound.

Preferably, the hydroxyl radicals of the radical S* are not substituted or are all substituted with the same group R' as previously defined, in particular with an acetyl group. Preferably, the optional amino group(s) $NR_bR_c$ of the radical S* denote(s) $NHR_b$ with $R_b$ all denoting a hydrogen atom or all denoting an acetyl group.

More preferentially, the hydroxyl radicals of the radical S* are not substituted, the optional amino group(s) $NR_bR_c$ of the radical S* denote(s) $NHR_b$ with $R_b$ all denoting a hydrogen atom or all denoting an acetyl group, and $R_3$ represents a hydrogen atom, a $(C_1-C_{18})$alkyl group, a $(C_2-C_{18})$alkenyl group or an acetyl group.

Preferably, S* denotes a monosaccharide sugar radical chosen from glucose and xylose. More particularly, S* denotes a sugar chosen from D-glucose and D-xylose, said radical S* being connected to the rest of the molecule (I) by a bond with the $C^1$ carbon atom of the sugar and this bond possibly being α or β anomeric Preferably, $R_3$ represents a hydrogen atom or an acetyl group, and $R_1$ represents a hydrogen radical or a linear or branched, saturated or unsaturated $C_1-C_{18}$, preferably $C_1-C_{16}$, alkyl such as methyl.

More preferentially, $R_3$ represents a hydrogen atom or an acetyl group, $R_1$ represents a hydrogen radical, and $R_2$ represents an aryl radical optionally substituted with a phenyl radical substituted with one or more groups chosen from methoxy, hydroxyl, carboxy, acetyloxy and/or benzyloxycarbonyl.

Particularly, S* denotes a monosaccharide sugar radical chosen from glucose and xylose, in particular chosen from D-glucose and D-xylose; $R_3$ represents a hydrogen atom; $R_1$ represents a hydrogen atom or a linear or branched, saturated or unsaturated $C_1-C_{18}$, preferably $C_1-C_{16}$, alkyl radical such as methyl; and $R_2$ denotes a radical of formula (B2):

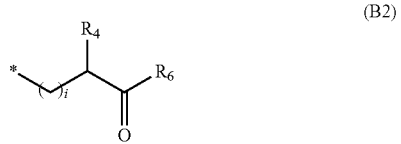

(B2)

in which
i=0 or 1,
$R_6$ represents an ethoxy, hydroxyl or $NH_2$ radical,
$R_4$ represents a hydrogen atom, and when i=0, $R_4$ represents a hydroxymethyl radical of formula (a5)

(a5)

or else $R_4$ can form, with $R_1$ and the nitrogen atom which bears $R_1$, a saturated heterocycle of formula A2:

A2

Particularly, S* denotes a monosaccharide sugar radical chosen from glucose and xylose, preferably having C3, and C4 and where appropriate C6 hydroxyl groups substituted with an acetyl group; $R_3$ represents a hydrogen atom; $R_1$ represents a hydrogen atom or a linear or branched, saturated or unsaturated $C_1-C_{18}$, preferably $C_1-C_{16}$, more preferentially $C_1-C_6$, alkyl radical such as methyl; and $R_2$ represents a radical (B2):

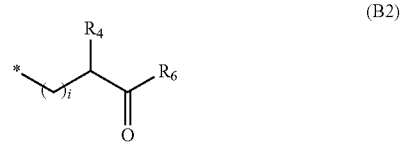

(B2)

in which i=0 or 1, $R_6$ represents a methoxy or ethoxy radical, $R_4$ represents a hydrogen atom, and when i=0, $R_4$ represents a hydroxymethyl radical of formula (a5)

(a5)

or else $R_4$ can form, with $R_1$ and the nitrogen atom which bears $R_1$, a saturated heterocycle of formula A2:

A2

For the purposes of the present invention and unless otherwise indicated:
the saturated or unsaturated and optionally fused rings may also be optionally substituted;
the "alkyl" radicals are saturated, linear or branched, generally $C_1-C_{18}$, particularly $C_1-C_{10}$, hydrocarbon-based radicals, preferably $C_1-C_6$ alkyl radicals; as $C_1-C_{14}$ alkyl group, mention may in particular be made of methyl, ethyl, isopropyl, n-propyl, n-butyl, t-butyl, isobutyl, sec-butyl, pentyl, isopentyl, neopentyl, n-hexyl, n-heptyl and octyl groups;
the "alkenyl" radicals are linear or branched, unsaturated $C_2-C_{18}$ hydrocarbon-based radicals; preferably comprising one or more conjugated or unconjugated double bonds, such as ethylene, propylene, butylene, pentylene, 2-methylpropylene, prenyl and decylene;
the "aryl" radicals are monocyclic or polycyclic, condensed or non-condensed carbon-based radicals preferentially comprising from 6 to 30 carbon atoms and at least one ring of which is aromatic; preferentially chosen from the aryl radical is a phenyl, biphenyl, naphthyl, indenyl, anthracenyl, and tetrahydronaphthyl; more preferentially aryl denotes phenyl; the "alkoxy" radicals are alkyloxy radicals with alkyl as previously defined and the alkyl part of the alkoxy is generally $C_1-C_{18}$, preferably $C_1-C_{10}$, such as methoxy, ethoxy, propoxy and butoxy; when unsaturated is mentioned, this implies that the alkoxy group can represent an alkenyloxy group with alkenyl as previously defined;

the "cycloalkyl" radicals are $C_4$-$C_8$ cycloalkyl radicals, preferably cyclopentyl and cyclohexyl radicals; the cycloalkyl radicals may be substituted cycloalkyl radicals, in particular substituted with alkyl, alkoxy, carboxylic acid, hydroxyl, amine and ketone groups;

the "heterocycloalkyl" radicals are saturated or partially unsaturated, nonaromatic heterocyclic radicals comprising from 4 to 8 ring members, which comprise from 1 to 3 heteroatoms, in particular chosen from oxygen, sulfur and nitrogen, preferably the morpholino, piperazino and piperidino radicals; the heterocycloalkyl radicals may be radicals which are substituted, in particular with alkyl, alkoxy, carboxylic acid, hydroxyl, amine and ketone groups;

the "aryl" or "heteroaryl" radicals can be substituted with at least one atom or group borne by at least one carbon atom, chosen from:

i) ($C_1$-$C_{10}$) and preferably $C_1$-$C_8$ alkyl optionally substituted with one or more radicals chosen from the following radicals: hydroxyl, optionally unsaturated ($C_1$-$C_4$)alkoxy, (poly)hydroxy($C_2$-$C_4$)alkoxy, acylamino, amino substituted with two identical or different $C_1$-$C_4$ alkyl radicals optionally carrying at least one hydroxyl group, or it being possible for the two radicals to form, with the nitrogen atom to which they are attached, a saturated or unsaturated and optionally substituted 5- to 7-membered and preferably 5- or 6-membered heterocycle optionally comprising another heteroatom identical to or different from nitrogen;

ii) halogen;

iii) hydroxyl;

iv) $C_1$-$C_4$ alkoxy;

v) $C_1$-$C_{10}$ alkoxycarbonyl;

vi) $C_2$-$C_4$ (poly)hydroxyalkoxy;

vii) $C_2$-$C_4$ alkylcarbonyloxy, preferentially —O-acetyl or acetyloxy;

viii) 5- or 6-membered heterocycloalkyl;

ix) 5- or 6-membered heteroaryl, optionally substituted with a ($C_1$-$C_4$)alkyl radical, preferentially methyl;

x) amino substituted with one or two $C_1$-$C_6$ alkyl radicals, which may be identical or different, optionally bearing at least: a) one hydroxyl group, b) amino optionally substituted with one or two optionally substituted $C_1$-$C_3$ alkyl radicals, said alkyl radicals possibly forming, with the nitrogen atom to which they are attached, a saturated or unsaturated, optionally substituted heterocycle comprising from 5 to 7 ring members, optionally comprising at least one other heteroatom possibly different from nitrogen, c) a quaternary ammonium group —$N^+R'R''R'''$, $Q^-$ for which R', R'' and R''', which may be identical or different, represent a hydrogen atom or a $C_1$-$C_4$ alkyl group; and $Q^-$ represents the anionic counterion such as the halide, d) a 5- or 6-membered heteroaryl radical optionally substituted with a ($C_1$-$C_4$) alkyl radical, preferentially methyl;

xi) acylamino (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical;

xii) carbamoyl (($R)_2$N—C(O)—) in which the R radicals, which may be identical or different, represent a hydrogen atom or a $C_1$-$C_4$ alkyl radical optionally bearing at least one hydroxyl group;

xiii) alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

xiv) aminosulfonyl (($R)_2$N—S(O)$_2$—) in which the R radicals, which may be identical or different, represent a hydrogen atom or a $C_1$-$C_4$ alkyl radical optionally bearing at least one hydroxyl group;

xv) carboxy in acid or salified form (preferably with an alkali metal or a substituted or unsubstituted ammonium);

xvi) cyano;

xvii) benzyloxycarbonyl;

xviii) polyhaloalkyl, preferentially trifluoromethyl;

xix) a phenylcarbonyloxy group optionally substituted with one or more hydroxyl groups; and xx) a phenyl group optionally substituted with one or more hydroxyl groups;

the "heteroaryl" radicals are radicals comprising, in at least one ring, one or more heteroatoms chosen in particular from O, N and S, preferably O or N, optionally substituted in particular with one or more alkyl, alkoxy, carboxyl, hydroxyl, amine or ketone groups, and at least one ring of which is aromatic. These rings may comprise one or more oxo groups on the carbon atoms of the heteroaryl; mention may in particular be made, among the heterocyclic radicals that may be used, of furyl, pyranyl, pyrrolyl, imidazolyl, pyrazolyl, pyridyl, thienyl and pyrimidinyl groups; optionally, the heterocyclic groups are fused groups, such as benzofuranyl, chromenyl, xanthenyl, indolyl, isoindolyl, quinolyl, isoquinolyl, chromanyl, isochromanyl, indolinyl, isoindolinyl, coumarinyl or groups, it being possible for these groups to be substituted, in particular with one or more OH groups;

the "protective group" or "PG" of the "hydroxyl" or "amino" function is known by those skilled in the art; mention may be made of the two books "*Protective Groups in Organic Synthesis*", T. W. Greene, published by John Wiley & Sons, N Y, 1981, pp. 193-217; "*Protecting Groups*", P. Kocienski, Thieme, 3rd ed., 2005.

In particular, the protective group is chosen from:

($C_1$-$C_6$)alkyl(thio)carbonyl such as formyl, acetyl or t-butylcarbonyl;

(di)(tri)halo($C_1$-$C_6$)alkyl(thio)carbonyl such as trifluoroacetyl (TFA);

($C_1$-$C_6$)alkoxy(thio)carbonyl such as methoxycarbonyl, ethoxycarbonyl, isobutyloxycarbonyl, t-butyloxycarbonyl (BOC), vinyloxycarbonyl, allyloxycarbonyl;

(di)(tri)halo($C_1$-$C_6$)alkoxy(thio)carbonyl such as 2,2,2-trichloroethylcarbonyl;

($C_1$-$C_6$)alkylthio-thiocarbonyl;

(di)(tri)halo($C_1$-$C_6$)alkylthiothiocarbonyl;

(di)($C_1$-$C_6$)(alkyl)aminocarbonyl;

(di)($C_1$-$C_6$)(alkyl)aminothiocarbonyl;

optionally substituted arylcarbonyl such as phenylcarbonyl or 2,4,6-trimethylphenylcarbonyl;

optionally substituted aryloxycarbonyl such as p-nitrophenoxycarbonyl;

optionally substituted aryl($C_1$-$C_6$)alkoxycarbonyl such as benzyloxycarbonyl or Cbz, p-methoxybenzyloxycarbonyl, 3,4-dimethoxybenzyloxycarbonyl, o-nitrobenzyloxycarbonyl, p-nitrobenzyloxycarbonyl, 2-bromobenzyloxycarbonyl (2-bromo-Z) and 2-chlorobenzyloxycarbonyl (2-chloro-Z), 4-nitrobenzyloxycarbonyl (nitro-Z), heteroaryl($C_1$-$C_6$)alkoxycarbonyl such as 9-fluorenyl-methoxycarbonyl (FMOC) or nicotinoyl;

(di)($C_1$-$C_6$)(alkyl)aminocarbonyl, for instance dimethyl-aminocarbonyl;

($C_1$-$C_6$)(alkyl)arylaminocarbonyl;

carboxyl;

optionally substituted aryl such as phenyl, dibenzosuberyl or 1,3,5-cycloheptatrienyl;

optionally substituted heteroaryl; in particular including the following cationic or non-cationic heteroaryl radicals comprising from 1 to 4 heteroatoms:

i) 5-, 6- or 7-membered monocyclic groups such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) 8- to 11-membered bicyclic groups such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$)alkyl, for instance methyl, or polyhalo($C_1$-$C_4$)alkyl, for instance trifluoromethyl;

iii) or the following tricyclic ABC group:

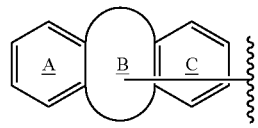

in which the two rings A and C optionally comprise a heteroatom, and ring B is a 5-, 6- or 7-membered ring, particularly a 6-membered ring, and contains at least one heteroatom, for instance piperidyl or pyranyl;

optionally cationic, optionally substituted heterocycloalkyl, the heterocycloalkyl group in particular representing a saturated or partially saturated 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl, di/tetrahydropyrimidinyl, these groups being optionally substituted with one or more groups such as ($C_1$-$C_4$)alkyl, oxo or thioxo, preferably tetrahydropyranyl THP; or the heterocycle represents the following group:

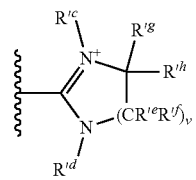

An⁻ which $R'^c$, $R'^d$, $R'^e$, $R'^f$, $R'^g$ and $R'^h$, which may be identical or different, represent a hydrogen atom or a ($C_1$-$C_4$)alkyl group, or alternatively two groups $R'^g$ with $R'^h$, and/or $R'^e$ with $R'^f$ form an oxo or thioxo group, or alternatively $R'^g$ with $R'^e$ together form a cycloalkyl; and v represents an integer between 1 and 3 inclusive; preferentially, $R'^c$ to $R'^h$ represent a hydrogen atom; and An⁻ represents a counterion;

isothiouronium —C(NR'^cR'^d)=N⁺R'^eR'^f; An⁻ with $R'^c$, $R'^d$, $R'^e$ and $R'^f$, which may be identical or different, representing a hydrogen atom or a ($C_1$-$C_4$)alkyl group; preferentially, $R'^c$ to $R'^f$ represent a hydrogen atom; and An⁻ represents a counterion;

isothiourea —C(NR'^cR'^d)=NR'^e; with $R'^c$, $R'^d$ and $R'^e$ as previously defined;

optionally substituted (di)aryl($C_1$-$C_4$)alkyl or triaryl($C_1$-$C_4$)alkyl such as 9-anthracenylmethyl, phenylmethyl (benzyl), diphenylmethyl or triphenylmethyl optionally substituted with one or more groups, in particular chosen from halogen, ($C_1$-$C_4$)alkyl, ($C_1$-$C_4$)alkoxy such as methoxy, hydroxyl, ($C_1$-$C_4$)alkylcarbonyl, (di)($C_1$-$C_4$)(alkyl)amino such as dimethylamino, nitro;

optionally substituted (di)heteroaryl($C_1$-$C_4$)alkyl or triheteroaryl($C_1$-$C_4$)alkyl, the heteroaryl group in particular being cationic or noncationic, 5- or 6-membered monocyclic comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl($C_1$-$C_4$)alkyl is (di)heteroarylmethyl or (di)heteroarylethyl;

$CR^1R^2R^3$ with $R^1$, $R^2$ and $R^3$, which may be identical or different, representing a halogen atom, such as (tri)(di)halo($C_1$-$C_4$)alkyl such as 2,2,2-trichloroethyl or a group chosen from:

($C_1$-$C_4$)alkyl such as methyl;

($C_1$-$C_4$)alkoxy;

optionally substituted aryl such as phenyl optionally substituted with one or more groups, for instance ($C_1$-$C_4$)alkyl, ($C_1$-$C_4$)alkoxy or hydroxyl;

optionally substituted heteroaryl such as thiophenyl, furanyl, pyrrolyl, pyranyl or pyridyl, optionally substituted with a ($C_1$-$C_4$)alkyl group;

$P(Z^1)R^{11}R^{12}R^{13}$ with $R^{11}$ and $R^{12}$, which may be identical or different, representing a hydroxyl, ($C_1$-$C_4$)alkoxy or alkyl group, $R^{13}$ representing a hydroxyl or ($C_1$-$C_4$)alkoxy group, and $Z^1$ representing an oxygen or sulfur atom;

($C_2$-$C_6$)alkylene, in particular allyl $H_2C=CH-CH_2-$;

optionally substituted arylsulfonyl such as p-toluenesulfonyl (Tos);

sterically hindered cycloalkyl such as the adamantyl group;

sterically hindered cycloalkyloxy(thio)carbonyl such as 1 adamantyloxycarbonyl (Adoc) or 1-(adamantyl)-1-methylethoxycarbonyl (Adpoc);

optionally substituted ($C_1$-$C_4$)alkoxy($C_1$-$C_4$)alkyl such as methoxymethyl (MOM), ethoxyethyl (EOM) and isobutoxymethyl;

(tri)(di)halo($C_1$-$C_4$)alkyl such as 2,2,2-trichloroethyl;

$R_eR_fR_gSi$— with $R_e$, $R_f$ et $R_g$, which may be identical or different, representing a ($C_1$-$C_6$)alkyl group, optionally substituted aryl group, optionally substituted (di)aryl ($C_1$-$C_4$)alkyl group, optionally substituted triaryl($C_1$-$C_4$)alkyl group, such as benzyl, in particular chosen from trimethylsilyl or TMS, triethylsilyl, isopropyldimethylsilyl, tert-butyldimethylsilyl or TBDMS, (triphenylmethyl)dimethylsilyl, t-butyldiphenylsilyl, methyldiisopropylsilyl, methyl(di-t-butyl)silyl, tribenzylsilyl, tri-p-xylylsilyl, triisopropylsilyl, triphenylsilyl;

or else two contiguous hydroxyl groups can be protected with an alkylene group *—C(R$^i$)(R$^m$)—(C(R$^k$)(R$^j$))$_q$—* as drawn below:

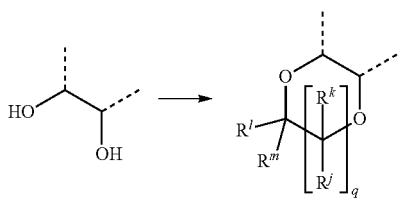

with R$^j$, R$^k$, R$^l$, and R$^m$, which may be identical or different, representing a hydrogen atom or a (C$_1$-C$_4$) alkyl, (poly)halo(C$_1$-C$_4$)alkyl, optionally substituted aryl such as phenyl, aryl(C$_1$-C$_4$)alkyl such as benzyl, (poly)halo(C$_1$-C$_4$)alkoxy, (C$_1$-C$_4$)alkoxy, halogen, (di)(C$_1$-C$_4$)(alkyl)amino or hydroxyl group, or else two R$^j$ and R$^k$ and/or R$^l$, and R$^m$ groups form, together with the carbon atom which bears them, an oxo group or a (hetero)cycloalkyl such as cyclohexyl or cyclopropyl; q is 0, 1, 2 or 3, preferably *—C(R$^i$)(R$^m$)—(C(R$^k$)(R$^j$))$_q$—* represents a methylene, ethylene, propylene, dimethylmethylene, *—C(CH$_3$)$_2$—* or diphenylmethylene *—C(Ph)$_2$-*, cyclopentylidene, cyclohexylidene, cycloheptylidene, benzylidene, p-methoxybenzylidene, 2,4-dimethoxybenzylidene, methoxymethylene and ethoxymethylene.

For the purposes of the present invention, the term "compound of formula (I)", or "compound of formulae (Ia$^1$), (Ia$^2$), (IBB), (Ib$^1$), (Ib$^2$) and/or (Ic)", or "compound 1 to 21" is intended to mean the compounds as defined in the present description, and also the solvates thereof such as hydrates, the optical and geometric isomers thereof, the tautomers thereof, and the organic or mineral base or acid salts thereof.

The acceptable solvates of the compounds used in the present invention comprise conventional solvates such as those formed during the last step of the preparation of said compounds due to the presence of solvents. Mention may be made, by way of example, of the solvates due to the presence of water (hydrates) or of linear or branched alcohols, such as ethanol or isopropanol.

The salts of the compounds (I) which comprise at least one acid function can be chosen from metal salts, for example aluminium (Al$^{3+}$), zinc (Zn$^{2+}$), manganese (Mn$^{2+}$) or copper (Cu$^{2+}$); alkali metal salts, for example lithium (Li$^+$), sodium (Na$^+$) or potassium (K$^+$); or alkaline-earth metal salts, for example calcium (Ca$^{2+}$) or magnesium (Mg$^{2+}$). They can also be ammonium derivatives of formula NH$_4^+$ or organic salts such as ammoniums of formula Y$_3$NH$^+$, NY$_3$ denoting an organic amine, the Y radicals being identical or different, it being possible for two or three Y radicals to form, in pairs, a ring with the nitrogen atom which carries them or it being possible for NY$_3$ to denote an aromatic amine. The organic amines are for example alkylamines, for instance methylamine, dimethylamine, trimethylamine, triethylamine or ethylamine, or hydroxyalkylamines, for instance 2-hydroxyethylamine, bis(2-hydroxyethyl)amine or tri-(2-hydroxyethyl)amine, or cycloalkylamines, for instance bicyclohexylamine or glucamine, piperidine, or pyridines and the like, for example collidine, quinine or quinoline, or amino acids which are basic in nature, for instance lysine or arginine.

The salts of the compounds of formula (I) which comprise at least one amine function can also be salts of an organic acid such as citric acid, lactic acid, tartaric acid, aspartic acid, glutamic acid, acetic acid, formic acid, trifluoroacetic acid, hydrochloric acid, glycolic acid or malic acid.

In the case where the compounds according to the invention are in salt form, the cations are of course in an amount which ensures the electro-neutrality of the compounds of formula (I).

The salts of the compounds of formula (I) according to the invention which comprise at least one acid function can advantageously be chosen from the metal salts Cu$^{2+}$, Mn$^{2+}$ and Zn$^{2+}$, the alkali metal salts Li$^+$, Na$^+$ and K$^+$ and the alkaline-earth metal salts Ca$^{2+}$ and Mg$^{2+}$.

According to another variant, the salts of the compounds of formula (I) according to the invention which comprise at least one acid function can advantageously be chosen from ammoniums, preferably from the salts of amino acids which are basic in nature, for instance lysine or arginine or from diethanolamine salts or triethanolamine salts.

Preferably, the compounds (I) which comprise at least one acid function are in the form of sodium salts Na$^+$.

Preferably, the compounds (I) which comprise at least one acid function are in the form of potassium salts K$^+$.

Preferably, the compounds (I) which comprise at least one acid function are in the form of calcium salts Ca$^{2+}$.

According to one particular embodiment of the invention, the compounds of formula (I) are such that, taken together or separately, R$_3$ represents a hydrogen atom, and R$_1$ represents a hydrogen atom or a (C$_1$-C$_{18}$)alkyl group, preferably methyl, and R$_2$ represents an aryl or heteroaryl radical, which is optionally substituted, preferably with one or more (C$_1$-C$_6$)alkyl, hydroxyl, C$_1$-C$_4$ alkoxy, C$_1$-C$_6$ alkoxycarbonyl, or carboxy groups, which may be identical or different.

According to this embodiment, S* also preferentially denotes a monosaccharide sugar radical chosen from glucose and xylose, in particular chosen from D-glucose and D-xylose.

According to another particular embodiment of the invention, the compounds of formula (I) are such that, taken together or separately, R$_3$ represents a hydrogen atom, and/or R$_1$ represents a hydrogen atom or a (C$_1$-C$_{18}$)alkyl group, preferably methyl, and/or R$_2$ represents a radical (B1) below:

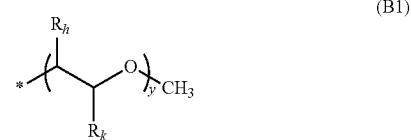

(B1)

in which:
R$_h$ and R$_k$, independently of one another, denote a hydrogen atom or a methyl radical, it being understood that R$_h$ and R$_k$ cannot simultaneously denote a methyl radical;
y=1 to 10, limits included.

According to this embodiment, S* also preferentially denotes a monosaccharide sugar radical chosen from glucose and xylose, in particular chosen from D-glucose and D-xylose.

According to another particular embodiment of the invention, the compounds of formula (I) are such that, taken together or separately, R$_3$ represents a hydrogen atom, and R$_1$ represents a hydrogen atom or a (C$_1$-C$_{18}$)alkyl group, preferably methyl, and R$_2$ represents the radical (B2) below:

in which:
  i=0 or 1;
  $R_4$ represents a hydrogen atom, or is chosen from the radicals (a1) to (a32) described below:

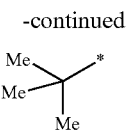

$R_4$ can also form, with $R_1$ and the nitrogen atom which bears $R_1$, a saturated heterocycle of formula A1, A2 or A3:

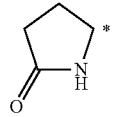

A1

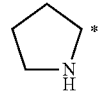

A2

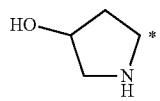

A3

$R_6$ denotes
  i) a hydroxyl radical —OH;
  ii) an alkoxide —O⁻, M⁺ with M⁺ representing a cation such as zinc ($Zn^{2+}$), manganese ($Mn^{2+}$), copper ($Cu^{2+}$) or iron ($Fe^{2+}$, $Fe^{3+}$), an alkali metal cation such as $Na^+$ or $K^+$, or an alkaline-earth metal cation such as $Mg^{2+}$ or $Ca^{2+}$, or an ammonium cation;
  iii) a saturated or unsaturated ($C_1$-$C_6$)alkoxy radical;
  iv) a radical —$NR_fR_g$ with $R_f$ and $R_g$, which may be identical or different, representing a hydrogen atom or a ($C_1$-$C_6$)alkyl group.

According to this embodiment, S* also preferentially denotes a monosaccharide sugar radical chosen from glucose and xylose, in particular chosen from D-glucose and D-xylose.

It is understood that, for the compounds of formula (I) as previously defined, when S* represents a monosaccharide radical, then it can be in pyranose form (the sugar heterocycle which constitutes it comprises 6 ring members) or furanose form (the sugar heterocycle which constitutes it comprises 5 ring members); and when S* represents a polysaccharide radical, it comprises the sequence of 2 to 5 saccharide units, which may be identical to or different from one another, which may be in furanose or pyranose form.

It is understood that, for the compounds of formula (I) as previously defined, when S* represents a polysaccharide radical, the polysaccharide is preferably a disaccharide which results from the linking of 2 pyranose units or the linking of one saccharide unit in furanose form and one unit in pyranose form or the linking of one saccharide unit in pyranose form and one unit in furanose form;

whether it is for the monosaccharide or polysaccharide radical, each saccharide unit can possibly be in the laevorotatory L form or the dextrorotatory D form, and in α or β anomeric form.

According to one preferred embodiment, the sugar radical S* represents a monosaccharide radical in which the heterocycle constituting it contains 4 or 5 carbon atoms, of formula S*' below:

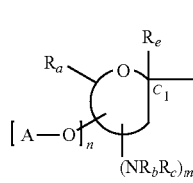

S*'

$R_a$ representing a hydrogen atom, a ($C_1$-$C_4$)alkyl group such as methyl or a (poly)hydroxy($C_1$-$C_4$)alkyl group such as hydroxymethyl or 1,2-dihydroxyethyl, the hydroxyl function(s) of the (poly)hydroxy($C_1$-$C_4$)alkyl group being substituted with A as defined below; it being understood that the $R_a$ radical is in the $C_5$ position if the sugar unit is in pyranose form or in the $C_4$ position if it is in furanose form;

$R_b$ representing a hydrogen atom or a ($C_1$-$C_4$)alkyl group, preferably hydrogen;

$R_c$ representing a hydrogen atom, or a protective group for the amine function, such as $R_d$—C(X')—, identical in the case of several hydroxyl functions, with X' representing an oxygen or sulfur atom, in particular an oxygen atom, and $R_d$ representing a ($C_1$-$C_4$)alkyl group, $R_c$ preferably representing an acetyl group $CH_3$—C(O)—;

$R_e$ representing a hydrogen atom or a —$CH_2$—O-A group; A representing a hydrogen atom, a ($C_1$-$C_6$)alkyl group or a hydroxyl-function-protecting group, such as $R_d$—C(X')— as defined above and in particular acetyl $CH_3$—C(O)—, or else, when n is greater than or equal to 2 and two groups A-O are contiguous, then two A groups can together form a linear or branched ($C_1$-$C_6$)alkylene chain;

preferably, all the protective groups for A are identical; n is equal to 1, 2 or 3 and m is equal to 0 or 1.

Preferably, m is 0.

According to another preferred embodiment, the sugar radical S* represents a polysaccharide radical constituted of 2 to 5 saccharide units, in particular of 2 to 3 and preferably of 2 saccharide units, linked together via an oxygen atom (oxy), 1→4 ($C_1$ of one saccharide unit →$C_4$ of the other saccharide unit) or 1→3 ($C_1$ of one saccharide unit →$C_3$ of the other saccharide unit) or 1→6 ($C_1$ of one saccharide unit →$C_6$ of the other saccharide unit), each saccharide unit of which is constituted of a heterocycle comprising 4 or 5 carbon atoms, of formula S*''' below:

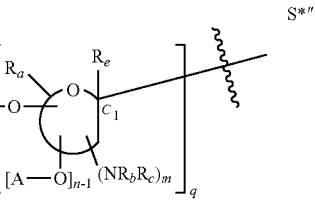

S*'' in which formula S*''' p and q represent integers of inclusively between 0 and 4 with p+q inclusively between 1 and 4, particularly between 1 and 2, preferentially p+q=1; $R_a$, which may be identical or different, are as defined previously, $R_b$, which may be identical or different, are as defined previously, $R_c$, which may be identical or different, are as defined previously, $R_e$, which may be identical or different, are as defined previously, A, which may be identical or different, are as defined previously, m, which may be identical or different, are as defined previously, n, which may be identical or different, are as defined previously, it being understood that the two sugar units between the square brackets q and p can be reversed, i.e. can represent the chain below:

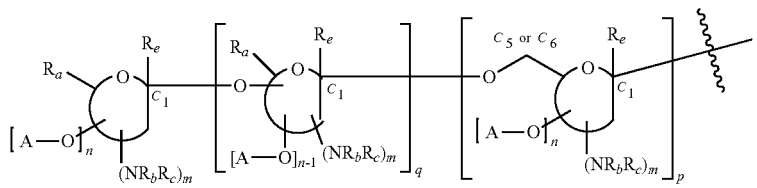

According to one preferred variant of the invention, the compounds of formula (I) are such that:

S* represents a monosaccharide sugar radical chosen from: glucose, galactose, mannose, xylose, lyxose, fucose, arabinose, rhamnose, quinovose, fructose, sorbose, talose, N-acetylglucosamine, N-acetylgalactosamine, glucosamine, galactosamine; or a disaccharide chosen from: lactose, maltulose, palatinose, lactulose, amygdalose, turanose, cellobiose, isomaltose, rutinose, maltose; more preferentially S* represents a monosaccharide sugar radical chosen from glucose and xylose, said radical S* comprising one or more radicals —$OR_s$ and optionally one or two —$NHR'_s$ radicals, more preferentially said radical S* comprising one or more radicals —$OR_s$, said monosaccharide or disaccharide radical being connected to the rest of the molecule by a bond between the $C^1$ carbon atom of the sugar or one of the sugars and this bond possibly being α or β anomeric;

$R_3$ represents:
i) a hydrogen atom;
ii) a ($C_1$-$C_{18}$)alkyl group, preferably ($C_1$-$C_6$)alkyl group such as methyl;
iii) a ($C_2$-$C_{18}$)alkenyl radical, preferably ($C_2$-$C_6$)alkenyl radical, such as prenyl;
iv) an aryl($C_1$-$C_4$)alkyl radical optionally substituted in particular with at least one hydroxyl and/or saturated or unsaturated ($C_1$-$C_4$)alkoxy group, in particular an aryl($C_1$-$C_4$)alkyl radical such as benzyl; or
v) a ($C_1$-$C_{18}$)alkylcarbonyl, preferably ($C_1$-$C_6$)alkylcarbonyl radical, in particular acetyl ($CH_3$—CO—);

$R_1$ represents a group chosen from:
i) a hydrogen atom; or
ii) a saturated or unsaturated ($C_1$-$C_{18}$)alkyl group, which is preferably saturated and more preferentially a saturated $C_1$-$C_6$ group such as methyl;

$R_2$ represents a group chosen from:
i) an aryl or heteroaryl radical, which is optionally substituted, preferably with one or more ($C_1$-$C_6$) alkyl, hydroxyl, $C_1$-$C_4$ alkoxy, $C_1$-$C_6$ alkoxycarbonyl, or carboxy groups, which may be identical or different; or (ii) a radical of formula (B1) below:

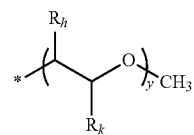

in which:
$R_h$ and $R_k$, independently of one another, denote a hydrogen atom or a methyl radical, it being understood that $R_h$ and $R_k$ cannot simultaneously denote a methyl radical;
y=1 to 10, preferably 1 to 3, limits included;

iii) a radical of formula (B2) below:

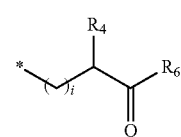

in which:
i=0 or 1;
$R_4$ represents a hydrogen atom, or is chosen from the radicals (a1) to (a32) described below:

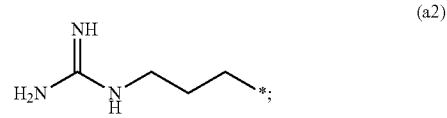

-continued
(a8) 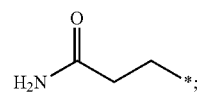
(a9) 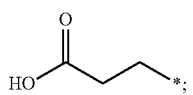
(a10) 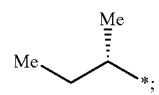
(a11) 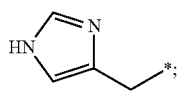
(a12) 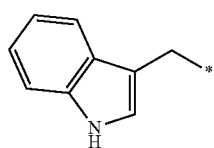
(a13) 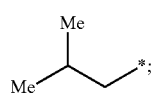
(a14) 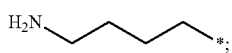
(a15) 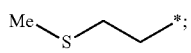
(a16) 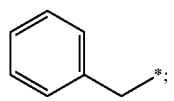
(a17) 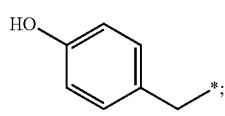
(a18) 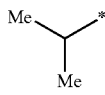
(a19) 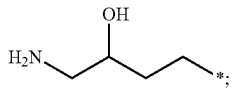
(a20) 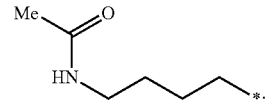
(a21) 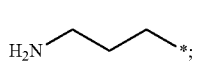
(a22) 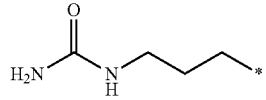
(a23) 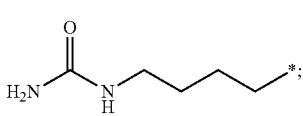
(a24) 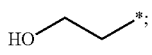
(a25) 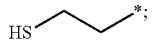
(a26) 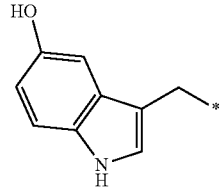
(a27) 
(a28) 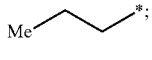
(a29) 
(a30) 
(a31) 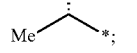
(a32) 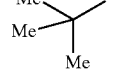
or $R_4$ can also form, with $R_1$ and the nitrogen atom which bears $R_1$, a saturated heterocycle of formula A1, A2 or A3:
A1 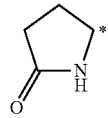
A2 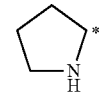
A3 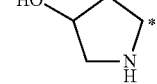
$R_6$ denotes
i) a hydroxyl radical —OH; or
ii) an alkoxide —O⁻, M⁺ with M⁺ representing a cation such as zinc ($Zn^{2+}$), manganese ($Mn^{2+}$), copper ($Cu^{2+}$) or iron ($Fe^{2+}$, $Fe^{3+}$), an alkali metal cation such as Na⁺ or K⁺, or an alkaline-earth metal cation such as $Mg^{2+}$ or $Ca^{2+}$, or an ammonium cation; or iii) a saturated or unsaturated ($C_1$-$C_6$)alkoxy radical; or iv) a radical —$NR_fR_g$ with $R_f$ and $R_g$, which may be identical or different, representing a hydrogen atom or a ($C_1$-$C_6$)alkyl group;

$R_s$ represents a hydrogen atom or a methyl radical or an acetyl radical;

said radicals $R_s$ preferably all being identical and preferably denoting a hydrogen atom or an acetyl radical;

$R'_s$ represents a radical chosen from a hydrogen atom or an acetyl radical.

More preferentially, the compounds of formula (I) are chosen from the compounds of formulae (I'), (I''), (I''''), (I'a), (I''a) and (I''''a) below:

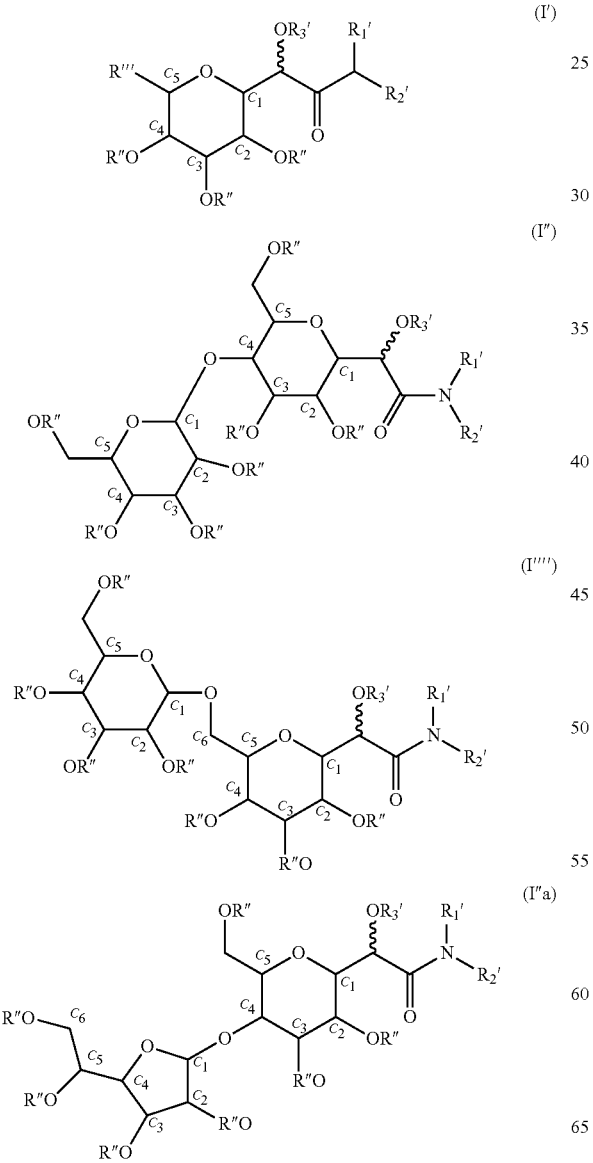

and also the solvates thereof such as hydrates, the optical and geometric isomers and tautomers thereof and the organic or mineral base or acid salts thereof, in which formulae (I'), (I''), (I''''), (I'a), (I''a) and (I''''a):

$R_1'$ has the same definition as that of $R_1$ for the compounds of formula (I); preferably $R'_1$ represents a hydrogen atom; a ($C_1$-$C_{18}$)alkyl radical, preferentially $C_1$-$C_4$ alkyl radical and more preferentially methyl; preferably $R_1'$ represents a hydrogen atom;

$R_2'$ has the same definition as that of $R_2$ for the compounds of formula (I); preferably $R'_2$ represents:
i) an aryl radical, which is optionally substituted, preferably with one or more groups, which may be identical or different, chosen from ($C_1$-$C_6$)alkyl, hydroxyl, $C_1$-$C_4$ alkoxy, $C_1$-$C_6$ alkoxycarbonyl, or carboxy; preferably $R_2'$ represents an aryl radical substituted with one or more methoxy and/or hydroxyl and/or carboxy;
ii) a radical (B'2) below:

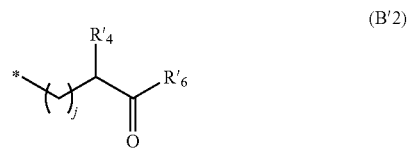

in which:
j=0 or 1;
$R'_4$ represents a hydrogen atom, or is chosen from the radicals (a1) to (a32) described below:

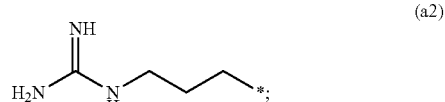

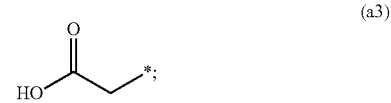

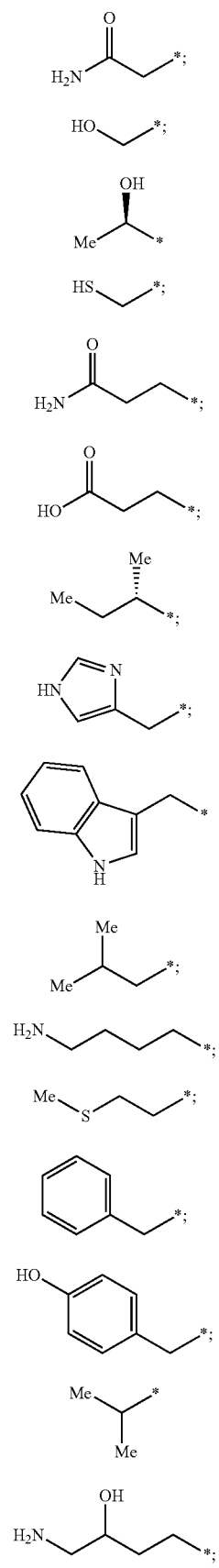
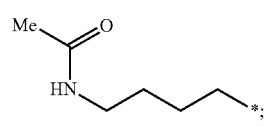 (a20)
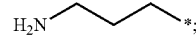 (a21)
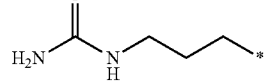 (a22)
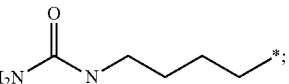 (a23)
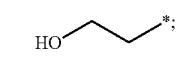 (a24)
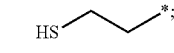 (a25)
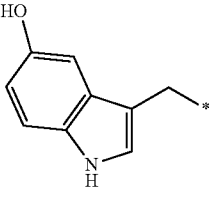 (a26)
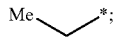 (a27)
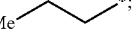 (a28)
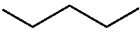 (a29)
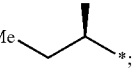 (a30)
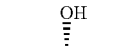 (a31)
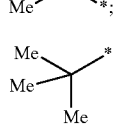 (a32)
$R'_4$ can also form, with $R'_1$ and the nitrogen atom which bears $R'_1$, a saturated heterocycle of formula A1, A2 or A3:
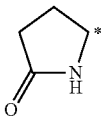 A1
 A2

-continued (A3)

HO—[pyrrolidine ring with N-H]—*

$R_6$ denotes
  i) a hydroxyl radical —OH; or
  ii) an alkoxide —O⁻, M⁺ with M⁺ representing a cation such as zinc ($Zn^{2+}$), manganese ($Mn^{2+}$), copper ($Cu^{2+}$) or iron ($Fe^{2+}$, $Fe^{3+}$), an alkali metal cation such as $Na^+$ or $K^+$, or an alkaline-earth metal cation such as $Mg^{2+}$ or $Ca^{2+}$, or an ammonium cation; or
  iii) a saturated or unsaturated ($C_1$-$C_6$)alkoxy radical; or
  iv) a radical —$NR_fR_g$ with $R_f$ and $R_g$, which may be identical or different, representing a hydrogen atom or a ($C_1$-$C_6$)alkyl group.
preferably, $R'_6$ represents OH; O⁻, M⁺; saturated ($C_1$-$C_6$) alkoxy, preferably methoxy or ethoxy, or $NH_2$;
$R_3'$ has the same definition as that of $R_3$ for the compounds of formula (I); preferably $R'_3$ represents a hydrogen atom or an acetyl radical, and preferably a hydrogen atom;
R" represents
  i) ($C_1$-$C_6$)alkyl; or
  ii) ($C_2$-$C_6$)alkenyl; or
  iii) an acetyl radical; or
  iv) a protective group (PG) for hydroxyl function(s), such as ($C_2$-$C_6$)alkyl(thio)carbonyl or benzyl; or
  v) a hydrogen atom;
preferably, R" represents a hydrogen atom or an acetyl radical; and preferably a hydrogen atom;
  R'" represents a hydrogen atom, or a ($C_1$-$C_4$)alkyl group, or a —$CH_2$—OR" group with R" as defined previously, in particular hydrogen or an acetyl radical, and preferably a hydrogen atom.

According to one particular embodiment, the compounds of the invention are of formula (I'). According to another particular embodiment of the invention, the compounds of the invention are of formula (I"). According to another particular embodiment of the invention, the compounds of the invention are of formula (I"").

According to another particular embodiment of the invention, the compounds of the invention are of formula (I'a). According to another particular embodiment of the invention, the compounds of the invention are of formula (I"a). According to another particular embodiment of the invention, the compounds of the invention are of formula (I""a).

According to one particular embodiment, S* and S*' represent a monosaccharide radical chosen from glucose, galactose, mannose, xylose, lyxose, fucose, arabinose, rhamnose, ribose, deoxyribose, quinovose, fructose, sorbose, talose, threose, erythrose, N-acetylglucosamine, N-acetylgalactosamine, glucosamine and galactosamine, and in particular S* and S*' represent a monosaccharide radical chosen from glucose and xylose.

In particular, S* and S*' represent a monosaccharide radical chosen from D-glucose, D-galactose, D-mannose, D-xylose, L-xylose, D-lyxose, L-lyxose, L-fucose, L-arabinose, D-arabinose, L-rhamnose, L-ribose, D-ribose, 2-deoxy-D-ribose, 2-deoxy-L-ribose, D-quinovose, D-fructose, L-sorbose, D-talose, D-threose, D-erythrose, L-threose, L-erythrose, N-acetyl-D-glucosamine, N-acetyl-D-galactosamine, D-glucosamine and D-galactosamine. Preferably, S denotes a monosaccharide chosen from D-glucose, D-galactose, D-mannose, D-xylose, D-lyxose, L-fucose, L-arabinose, L-rhamnose, D-ribose, 2-deoxy-D-ribose, D-quinovose, D-fructose, L-sorbose, D-talose, D-threose, D-erythrose, N-acetyl-D-glucosamine, N-acetyl-D-galactosamine, D-glucosamine and D-galactosamine, and in particular S* and S*' represent a monosaccharide radical chosen from D-glucose and D-xylose.

Advantageously, S* and S*' represent a monosaccharide radical chosen from glucose, xylose, rhamnose, mannose and galactose or a disaccharide chosen from lactose, maltose and cellobiose. In particular, S* denotes a monosaccharide chosen from D-glucose, D-xylose, L-rhamnose, D-mannose and D-galactose or a disaccharide chosen from D-lactose, D-maltose and D-cellobiose.

Preferably, S* and S*' represent a sugar chosen from glucose, xylose and lactose.

More particularly, S* and S*' denote a sugar chosen from D-glucose, L-xylose and D-lactose. Preferentially, S* and S*' denote glucose or xylose. In particular, S* and S*' denote D-glucose or D-xylose.

According to another particular embodiment, S* and S*'" represent a polysaccharide and in particular a disaccharide chosen from lactose, maltulose, palatinose, lactulose, amygdalose, turanose, cellobiose, isomaltose, rutinose and maltose.

According to one particular embodiment, the radicals S* and S*'" represent a polysaccharide and in particular a disaccharide chosen from D-lactose, maltulose, palatinose, lactulose, amygdalose, D-turanose, D-cellobiose, isomaltose, rutinose and D-maltose.

According to another particular embodiment, $R_2$ and $R_2'$ represent respectively a radical (B2), respectively (B'2) such as:

(B2)

*—(CH)$_i$—CH($R_4$)—C(=O)—$R_6$ or (B'2)

*—(CH)$_j$—CH($R'_4$)—C(=O)—$R'_6$ in which:
  i=0 or 1; j=0 or 1;
  $R_4$ and $R'_4$ independently represent a hydrogen atom or are independently chosen from the radicals (a1) to (a32) described below:

(a1)

Me—*;

(a2)

$H_2N$—C(=NH)—NH—CH$_2$CH$_2$CH$_2$—*;

(a3)

HO—C(=O)—CH$_2$—*;

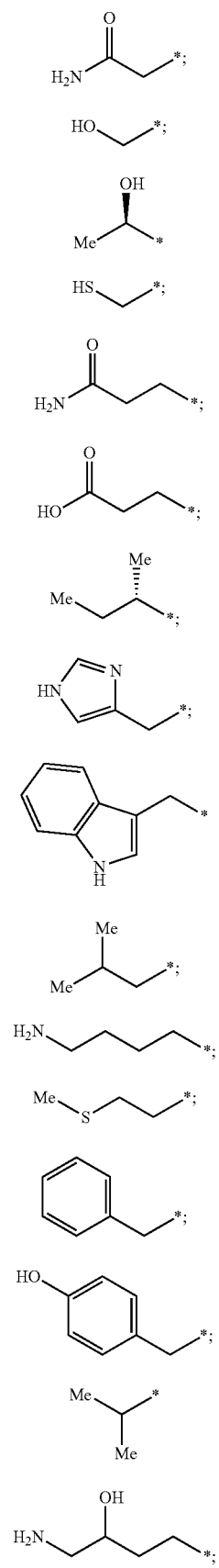
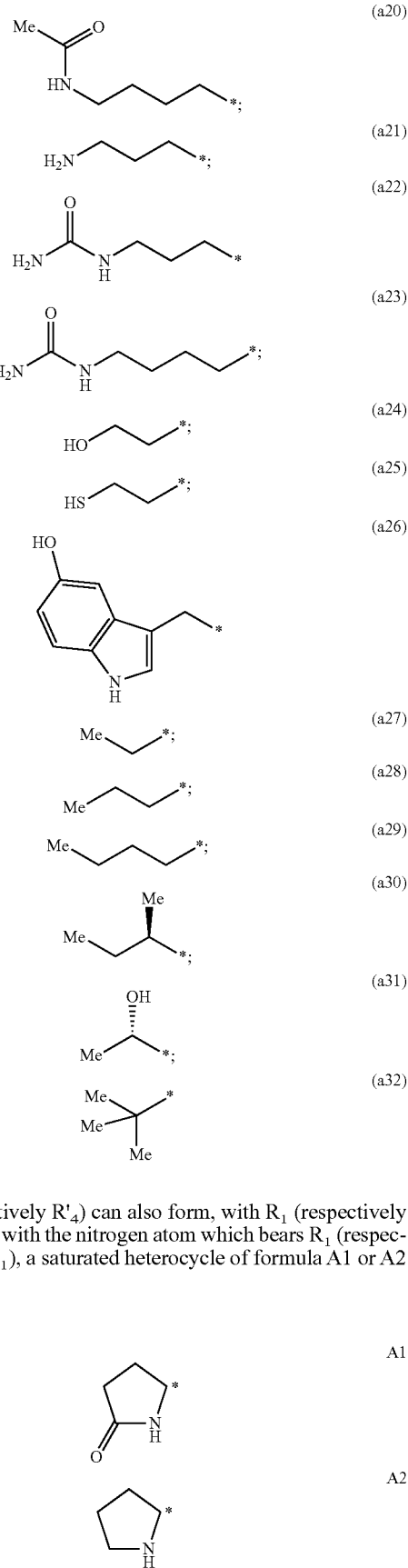
$R_4$ (respectively $R'_4$) can also form, with $R_1$ (respectively $R'_1$) and with the nitrogen atom which bears $R_1$ (respectively $R'_1$), a saturated heterocycle of formula A1 or A2 or A3:

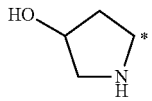

A3

$R_6$ and $R'_6$ independently denote
  i) a hydroxyl radical —OH; or
  ii) an alkoxide —O⁻, M⁺ with M⁺ representing a cation such as zinc ($Zn^{2+}$), manganese ($Mn^{2+}$), copper ($Cu^{2+}$) or iron ($Fe^{2+}$, $Fe^{3+}$), an alkali metal cation such as $Na^+$ or $K^+$, or an alkaline-earth metal cation such as $Mg^{2+}$ or $Ca^{2+}$, or an ammonium cation; or
  iii) a saturated or unsaturated ($C_1$-$C_6$)alkoxy radical; or
  iv) a radical —$NR_fR_g$ with $R_f$ and $R_g$, which may be identical or different, representing a hydrogen atom or a ($C_1$-$C_6$)alkyl group.

Preferably,
$R_4$ and $R'_4$ represent a hydrogen atom when i=1 or j=1, and when i=1 or j=0, $R_4$ and $R'_4$ independently represent a hydrogen atom or a hydroxymethyl radical (a5): chosen from:

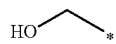

(a5)

$R_4$ can form, with $R_1$ and the nitrogen atom which bears $R_1$, a saturated heterocycle of formula A2:

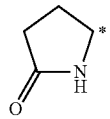

A2

Novel Compounds

A subject of the invention is also the compounds of formula (I) as previously defined, with the exception of the compound (D) below:
RN=[1087698-42-7]

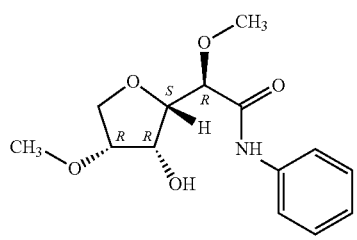

In particular, a subject of the invention is the novel compounds of formulae (Ia¹), (Ia²), (IBB), (Ib¹) and (Ib²) and/or (Ic), as defined below.

Thus, the invention relates to the novel compounds of formula (Ia¹), and also the solvates and/or isomers and/or salts thereof:

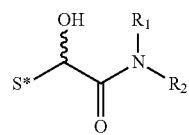

(Ia¹)

in which formula (Ia¹) S*, $R_1$ and $R_2$ are as previously defined.

Among the compounds of structure (Ia¹), $R_2$ denotes in particular an aryl or heteroaryl radical, which is optionally substituted (as defined above).

Preferably, S* denotes a sugar radical chosen from glucose or xylose. More particularly, S* denotes a sugar radical chosen from D-glucose or D-xylose.

Preferably, the hydroxyl groups of S* are not substituted and the optional amino groups NRbRc are such that Rb and Rc independently denote a hydrogen atom or an acetyl radical.

Preferably, $R_1$ denotes a hydrogen atom or a $C_1$-$C_4$ alkyl group and more preferentially methyl. Preferentially, $R_1$ denotes a hydrogen atom.

Preferably, $R_2$ denotes an optionally substituted aryl radical. More preferentially, $R_2$ denotes a phenyl radical, preferably substituted with one or more groups, which may be identical or different, chosen from: ($C_1$-$C_6$)alkyl, hydroxyl, $C_1$-$C_4$ alkoxy, $C_1$-$C_6$ alkoxycarbonyl, or carboxy.

In the case of a carboxy group, said group can also be in the form of a salt (carboxylate)COO⁻M⁺, with M⁺ representing a cation such as zinc ($Zn^{2+}$), manganese ($Mn^{2+}$), copper ($Cu^{2+}$) or iron ($Fe^{2+}$,$Fe^{3+}$), an alkali metal cation such as $Na^+$ or $K^+$ or an alkaline-earth metal cation such as $Mg^{2+}$ or $Ca^{2+}$, or an ammonium cation.

In particular, $R_2$ represents a phenyl radical substituted with one or more methoxy and/or hydroxyl and/or carboxy groups.

Among the novel compounds of formula (Ia¹), the compound 1 (and/or solvates thereof and/or salts thereof) is particularly preferred:

| S* | compound | structure |
|---|---|---|
| D-glucose | 1 |  Chiral |

The invention also relates to the novel compounds of formulae (Ia²), and also the solvates and/or isomers and/or salts thereof:

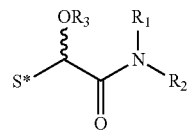

(Ia²)

in which formula (Ia²) S*, $R_1$, $R_2$, and $R_3$ are as previously defined, with the proviso that the hydroxyl groups of S* are substituted with the same radical as the radical $R_3$. ($R'=R_3$ and $R_3$ does not represent a hydrogen atom).

Among the compounds of structure (Ia²), mention may in particular be made of the compounds for which $R_2$ denotes an aryl or heteroaryl radical, which is optionally substituted (as previously indicated in the definitions of the radicals).

Among the compounds of structure (Ia²), mention may in particular be made of the compounds for which S* denotes a sugar chosen from glucose or xylose. More particularly, S* denotes a sugar chosen from D-glucose or D-xylose.

The compounds of structure (Ia²) are in particular such that $R_3$ represents an acetyl group, the hydroxyl groups of S* and the optional amino groups are substituted with an acetyl group (—CO—CH$_3$) ($R_3=R'=R_c=$acetyl, and $R_b=$H).

The compounds of formula (Ia²) are in particular such that $R_1$ denotes a hydrogen atom or a $C_1$-$C_4$ alkyl group such as methyl. Preferentially, $R_1$ denotes a hydrogen atom.

Preferably, $R_2$ denotes an aryl radical. More preferentially, $R_2$ denotes a phenyl radical, preferably substituted with one or more groups, which may be identical or different, chosen from: ($C_1$-$C_6$)alkyl, $C_1$-$C_4$ alkoxy, $C_2$-$C_4$ alkylcarbonyloxy, preferentially —O-acetyl or acetyloxy (CH$_3$—CO—O—), benzyloxycarbonyl, or carboxy. In the case of a carboxy group, said group can also be in the form of a salt (carboxylate)COO$^-$M$^+$, with M$^+$ representing a cation such as zinc (Zn$^{2+}$), manganese (Mn$^{2+}$), copper (Cu$^{2+}$) or iron (Fe$^{2+}$,Fe$^{3+}$), an alkali metal cation such as Na$^+$ or K$^+$ or an alkaline-earth metal cation such as Mg$^{2+}$ or Ca$^{2+}$, or an ammonium cation.

In particular, $R_2$ represents a phenyl radical substituted with one or more methoxy and/or acetyloxy and/or benzyloxycarbonyl and/or carboxy and more particularly acetyloxy and/or benzyloxycarbonyl and/or carboxy radicals.

Among the compounds of formula (Ia²), the novel compounds 2 and 3 (and/or solvates thereof and/or salts thereof) are more particularly preferred:

The invention also relates to the novel compounds of formula (IBB):

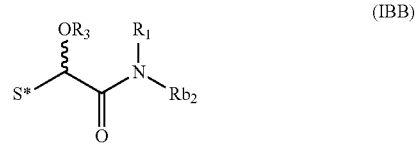

(IBB)

in which S*, $R_1$, and $R_3$ have the same meaning as in formula (I).

$Rb_2$ represents i) a substituted phenyl radical or an optionally substituted heteroaryl radical; or (ii) a radical of formula (B1):

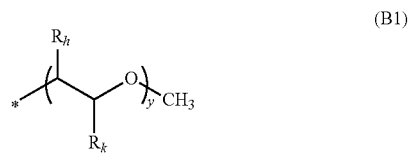

(B1)

in which:

$R_h$ and $R_k$, independently of one another, denote a hydrogen atom or a methyl radical, it being understood that $R_h$ and $R_k$ cannot simultaneously denote a methyl radical;

y=1 to 10, limits included;

| S* | compound | structure |
|---|---|---|
| D-glucose | 2 | ![structure 2] |
| D-glucose | 3 | ![structure 3] | iii) a radical of formula (B2):

$$\overset{*}{\underset{}{\phantom{X}}}(\phantom{X})_i\overset{R_4}{\underset{}{\phantom{X}}}\overset{}{\underset{O}{C}}R_6 \quad (B2)$$

in which:

i=0 or 1;

$R_4$ represents a hydrogen atom or a radical chosen from the radicals (a1) to (a32) described below:

-continued

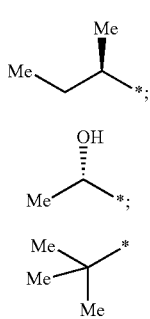

(a30)

(a31)

(a32)

$R_4$ can form, with $R_1$ and the nitrogen atom which bears $R_1$, a saturated heterocycle of formula A1, A2 or A3:

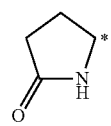

A1

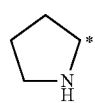

A2

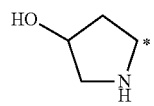

A3

$R_6$ denotes
  i) a hydroxyl radical —OH;
  ii) an alkoxide —O⁻, M⁺ with M⁺ representing a cation such as zinc ($Zn^{2+}$), manganese ($Mn^{2+}$), copper ($Cu^{2+}$) or iron ($Fe^{2+}$, $Fe^{3+}$), an alkali metal cation such as $Na^+$ or $K^+$, or an alkaline-earth metal cation such as $Mg^{2+}$ or $Ca^{2+}$, or an ammonium cation;
  iii) a saturated or unsaturated ($C_1$-$C_6$)alkoxy radical;
  iv) a radical —$NR_fR_g$ with $R_f$ and $R_g$, which may be identical or different, representing a hydrogen atom or a ($C_1$-$C_6$)alkyl group.

Among the compounds of formula (IBB), mention may particularly be made of the compounds for which S* denotes a sugar radical chosen from glucose or xylose and more particularly the compounds for which S* denotes a sugar radical chosen from D-glucose or D-xylose.

According to one particular form of the invention, the novel compounds of formula (IBB) are compounds of formula (Ib¹), and also solvates and/or isomers and/or salts thereof:

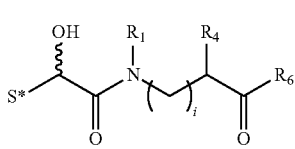

(Ib¹)

in which formula (Ib¹) S*, $R_1$, $R_4$, $R_6$ and i are as previously defined.

In particular, the compounds of formula (Ib¹) are such that S* denotes a sugar radical chosen from glucose or xylose and more particularly those for which S* denotes a sugar radical chosen from D-glucose or D-xylose.

Preferably, the hydroxyl groups of S* are not substituted and the optional amino groups NRbRc are such that Rb and Rc independently denote a hydrogen atom or an acetyl radical.

Preferably, $R_1$ denotes a hydrogen atom or a $C_1$-$C_4$ alkyl group and more particularly methyl. Preferentially, $R_1$ denotes a hydrogen atom.

Preferably, $R_6$ denotes a hydroxyl group or forms, with the carbonyl group in the alpha position, a carboxylate radical COO⁻M⁺ with M⁺ as previously defined, or else $R_6$ denotes a ($C_1$-$C_4$) alkoxy radical such as methoxy or ethoxy, or $R_6$ denotes a radical $NH_2$.

Preferably, i=0.

Preferably, $R_4$ represents a hydrogen atom when i=1, and when i=0, $R_4$ represents a hydrogen atom or a hydroxymethyl radical (a5)

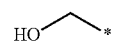

(a5)

or else $R_4$ forms, with $R_1$ and the nitrogen atom which bears $R_1$, a saturated heterocycle of formula A2:

A2

Among the compounds of structure (IBB) and of structure (Ib¹), mention may in particular be made of the compounds 4 to 12 (and/or solvates thereof and/or salts thereof):

| S* | compound | structure |
|---|---|---|
| D-glucose | 4 | |
| D-glucose | 5 | |
| D-glucose | 6 | |

-continued

| S* | compound | structure |
|---|---|---|
| D-glucose | 7 | (structure) |
| D-glucose | 9 | (structure) |
| D-xylose | 10 | (structure) |
| D-xylose | 11-dia1 | (structure) |
| D-xylose | 11-dia2 | (structure) |
| D-xylose | 12 | (structure) |
| D-xylose | 13 | (structure) |

Among the novel compounds of structure (IBB), mention may be made of the compounds of formula (Ib²), and also the solvates and/or isomers and/or salts thereof:

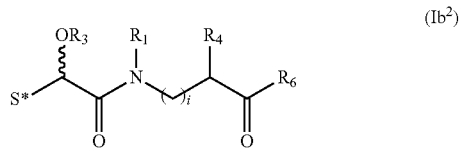

(Ib²)

in which formula (Ib²) S*, $R_1$, $R_3$, $R_4$, $R_6$, and i are as previously defined, with the proviso that the hydroxyl groups of S* are all substituted with the same group as in $R_3$ (R'=$R_3$ and $R_3$ does not represent a hydrogen atom), with the exception of the hydroxyl group at C2 of S* which remains in free form (—OH).

In particular, the compounds of formula (Ib²) are such that S* denotes a sugar radical chosen from glucose or xylose and more particularly such that S* denotes a sugar radical chosen from D-glucose or D-xylose.

Preferably, $R_3$ represents an acetyl group, and the hydroxyl groups of S* and the optional amino groups are substituted with an acetyl group (—CO—$CH_3$) ($R_3$=R'=$R_c$=acetyl, and $R_b$=H), except the hydroxyl group at C2 which remains in free form (—OH).

Preferably, $R_1$ denotes a hydrogen atom or a $C_1$-$C_4$ alkyl group and more preferentially methyl. Preferentially, $R_1$ denotes a hydrogen atom or a methyl radical.

Preferably, $R_6$ denotes a ($C_1$-$C_4$) alkoxy group and more particularly a methoxy or ethoxy, preferentially ethoxy, radical, or $R_6$ denotes an amino radical —$NH_2$.

Preferably, i=0.

Preferably, $R_4$ represents a hydrogen atom when i=1, and when i=0, $R_4$ represents a hydrogen atom or a hydroxymethyl radical (a5):

(a5)

or else $R_4$ forms, with $R_1$ and the nitrogen atom which bears $R_1$, a saturated heterocycle of formula A2:

A2

Among the novel compounds of formula (IBB) and of formula (Ib²), mention may in particular be made of the compounds 14 to 21 (and/or solvates thereof and/or salts thereof):

| S* | compound | structure |
|---|---|---|
| D-glucose | 14 | |
| D-glucose | 15 | |
| D-glucose | 16 | |
| D-glucose | 17 | |
| D-glucose | 18 | |

| S* | compound | structure |
|---|---|---|
| D-xylose | 19 | |
| D-xylose | 20-dia1 | |
| D-xylose | 20-dia2 | |
| D-xylose | 21 | |

Among the novel compounds of formula (IBB), mention may also be made of the compounds pounds of formula (Ic), and also the solvates and/or isomers and/or salts thereof:

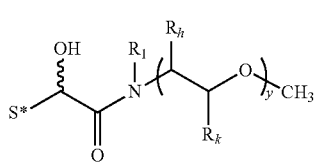

(Ic)

in which formula (Ic) S*, $R_1$, $R_h$, $R_k$ and y are as previously defined for the compounds of formula (I).

Preferably, the hydroxyl groups of S* are not substituted and the optional amino groups —NRbRc are such that Rb and Rc independently denote a hydrogen atom or an acetyl radical.

Preferably, y is between 1 and 5, more preferentially between 1 and 3, limits included.

The preferred novel compounds are the compounds 1 to 21 previously described.

Process for preparing the compounds of formula (I), in particular (Ia¹), (Ia²), (Ib¹), and (Ib²), (Ic), of the invention Another subject of the invention is a process for preparing, or a process for the chemical synthesis of, the compounds of formula (I) as previously defined, according to scheme (1) below:

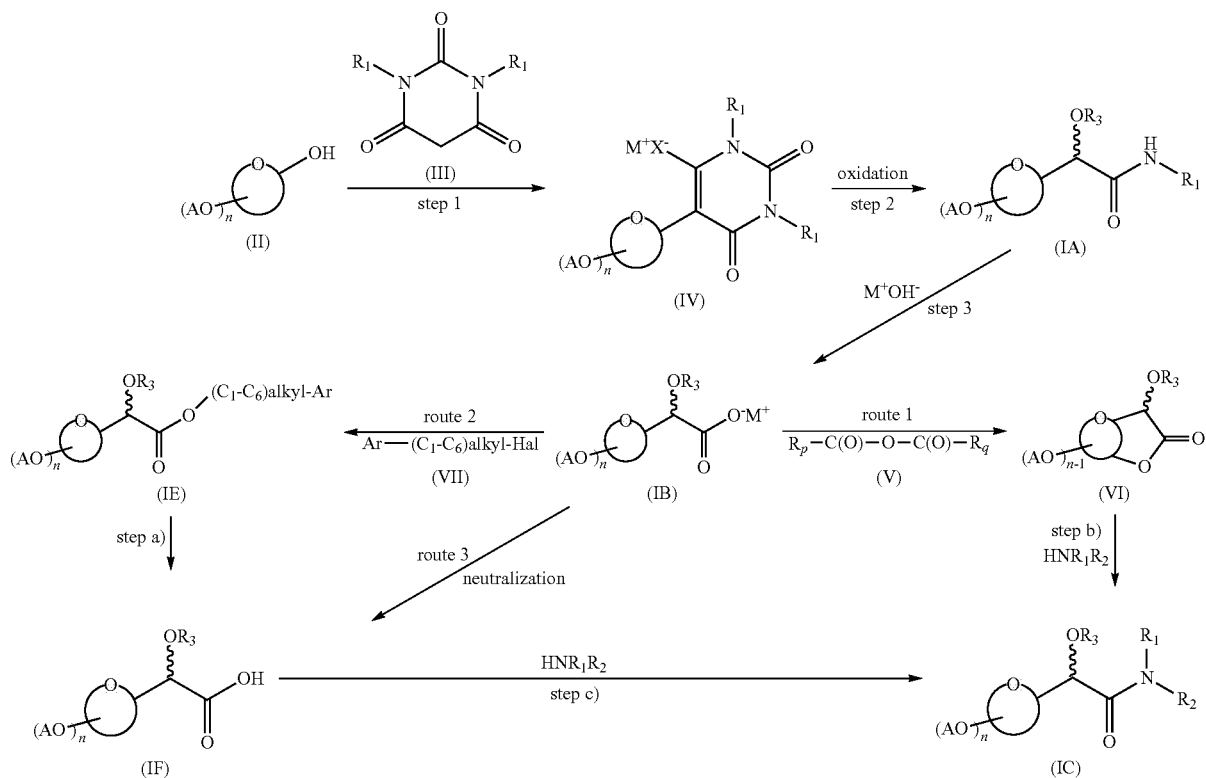

which preparation process comprises the following steps:
- step 1 which consists in reacting a monosaccharide or a polysaccharide of formula (II) with a barbituric acid derivative (III), in particular in the presence of a mineral base such as M⁺OH⁻, M⁺ representing a cation such as Na⁺ or K⁺, or preferably in the presence of a weak base such as (bi)carbonate, in particular with alkali metal (bi)carbonate, or in the presence of an organic base such as triethylamine or diisopropylethylamine,
- step 1 which is carried out in particular in a polar protic solvent such as water, by heating optionally at a temperature between 30° C. and 100° C., in particular at 80° C., preferably for a period of between 1 hour and 24 hours, in particular between 3 hours and 10 hours, such as 5 hours, so as to give the compound comprising a sugar unit (IV);
- step 2 which subsequently consists in reacting the compound (IV) with a chemical oxidizing agent such as

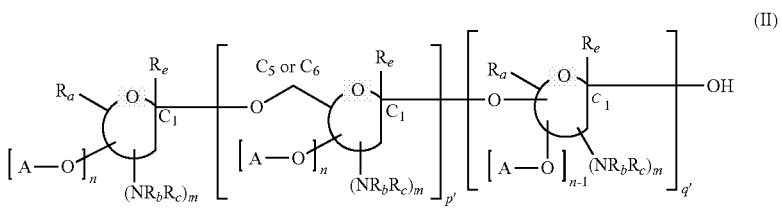

(II)

in which formula (II) A, $R_a$, $R_b$, $R_c$, $R_e$, n, and m are as previously defined, p' and q' representing an integer inclusively between 0 and 4, with p'+q' inclusively between 0 and 4, in particular between 0 and 2, preferably p'+q'=0 or 1, it being understood that the two units between square brackets can be reversed; the compound of formula (II) being represented in the scheme by:

hydrogen peroxide or a hydrogen peroxide-generating agent such as oxone, in particular in a polar solvent with a boiling point of between 40° C. and 100° C. at atmospheric pressure, such as acetone or acetonitrile, or a polar protic solvent such as water, optionally in a basic medium and/or in the presence of a chelating agent such as ethylenediaminetetraacetic acid (EDTA) optionally in salt form, optionally by heating to a temperature of between 30° C. and 70° C., so as to give an amide C-glycoside compound (IA), 1) if $R_3$ represents a hydrogen atom and it is desired for it to represent a $(C_1-C_{18})$alkyl, $(C_2-C_{18})$alkenyl or $(C_2-C_{18})$alkynyl group, or for the OH group to be protected, then an alkylation step or a step of protecting the hydroxyl function is carried out, if on the other hand $R_3$ represents PG, then it can be deprotected if it is desired to obtain a free hydroxyl function, 2) if A represents a hydrogen atom and it is desired to have a PG, then a protection step is added, 3) if $R_b$ and $R_c$ of $NR_bR_c$ represent hydrogen atoms and it is desired to protect the amino group(s), a protection step is carried out, step 3 which subsequently consists in reacting the amide compound (IA) with a base $OH^-M^+$ as previously defined so as to give a C-glycoside carboxylate compound (IB); said compound (IB) can then follow 3 synthetic routes:

route 1 which consists in reacting an anhydride (V) of formula $R^p$—C(O)—O—C(O)—$R^q$ with $R^p$ and $R^q$, which may be identical or different, representing a $(C_1-C_4)$alkyl group such as methyl (such that the anhydride is acetic anhydride), with the compound (IB) so as to give by intramolecular reaction between the oxygen atom of the group A-O at $C^2$ of the first sugar unit directly connected to the rest of the molecule on the C═O after elimination of water so as to give the compound (VI), this compound possibly subsequently reacting according to step b) with an amine $R_1R_2NH$ so as to give the amide C-glycoside (IC);

route 2 which consists in reacting the compound (IB) with an arylalkyl halide (VII): Ar($C_1$-$C_6$)alkyl-Hal with Ar representing an aryl and Hal denotes a halide chosen from Cl, Br, F and I, preferably (VII) represents a benzyl halide such as benzyl bromide, so as to give the ester C-glycoside (IE); this compound possibly subsequently reacting according to step a) by dealkylarylation (debenzylation) such as by catalytic reduction, for instance hydrogenation with palladium-on-graphite so as to give the acid C-glycoside (IF); this compound possibly subsequently reacting according to step c) with an amine $R_1R_2NH$ so as to give the amide C-glycoside (IC);

route 3 which consists in neutralizing (IB) with an organic or mineral acid: so as to give the acid C-glycoside (IF); it is understood that, depending on the desires for substituents on the radicals R', A and $NR_bR_c$, options 1) to 3) mentioned in step 2 also apply to routes 1 and 2 and to steps a), b) and c); preferably, the same GP is used for the entire molecule, the compounds (IC) being contained in formula (I) according to the invention.

It is also understood that, during the preparation of the reagent (II), steps 2) and 3) mentioned above can be applied thereto.

Thus, for example, when the saccharide (II) is a D-glucose, the scheme for synthesizing the corresponding amides (IC) (IC)gluc is as follows:

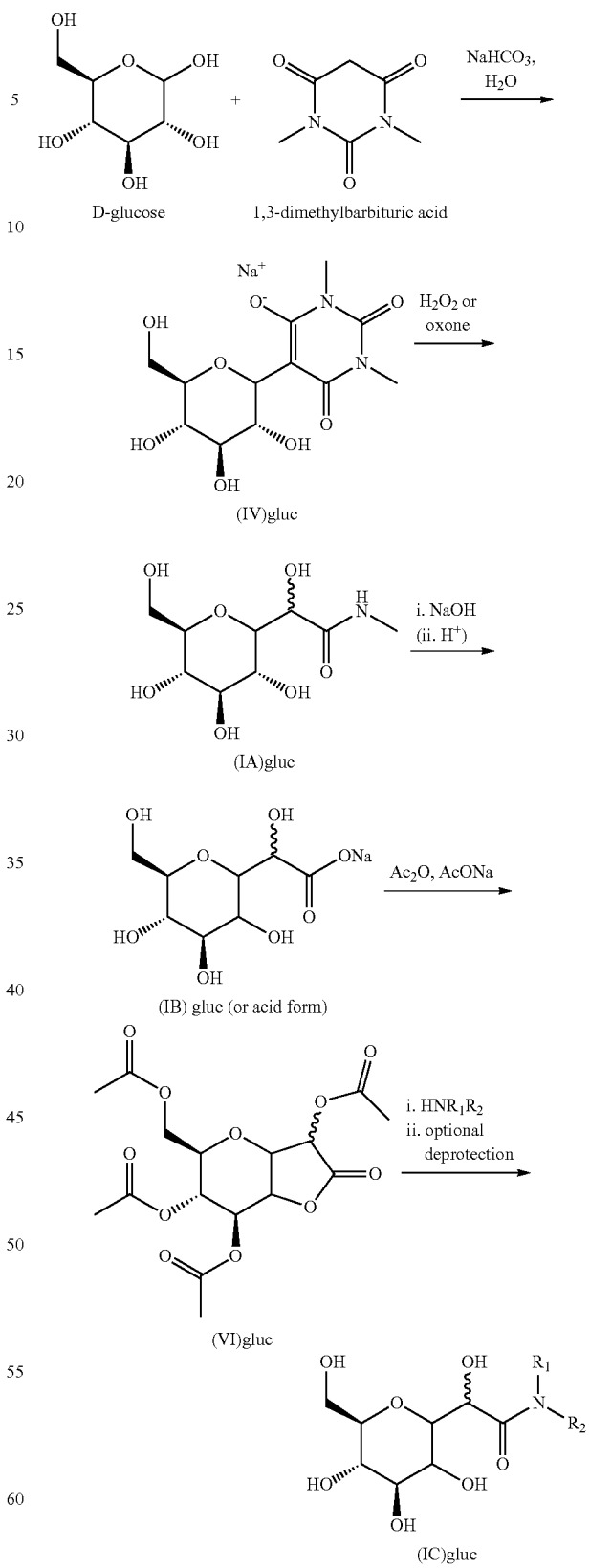

In this scheme, the intermediate (IB)gluc or the corresponding acid form obtained after acidification in particular denotes the compound (IB)glucose below:

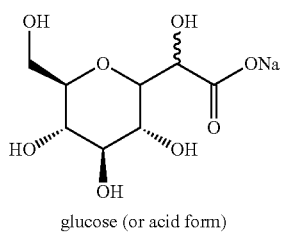

glucose (or acid form) (IB)

the compound (VI)gluc in particular denotes the compound (VI)glucose below:

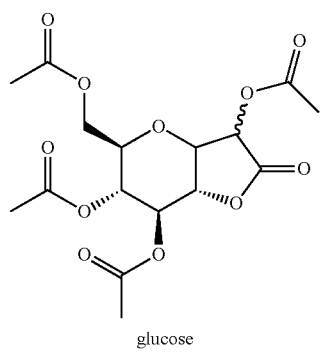

glucose (VI)

and the compound (IC) in particular denotes the compound (IC)glucose below:

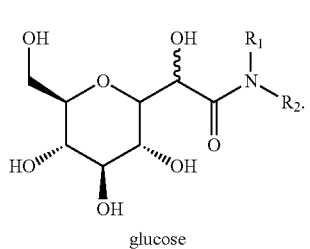

glucose (IC)

According to the same principle, when the saccharide (II) is a D-xylose, the scheme for synthesizing the corresponding amides (IC) (IC)xyl is as follows:

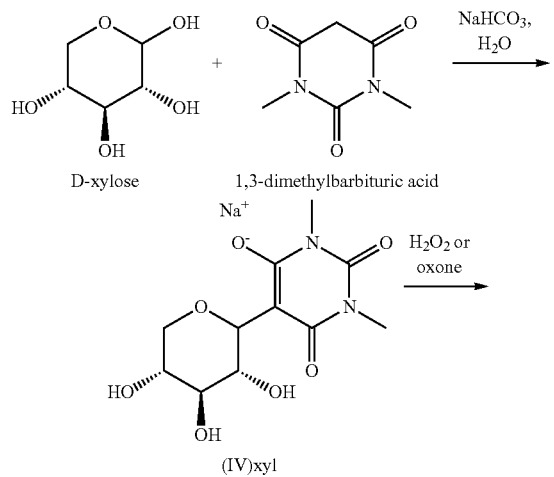

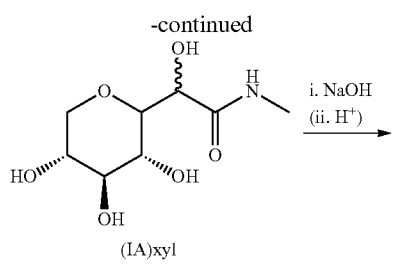

(IA)xyl

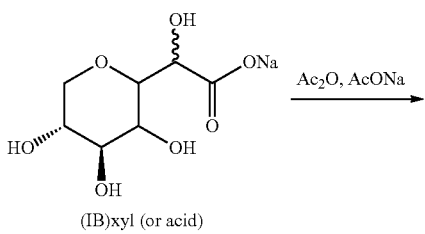

(IB)xyl (or acid)

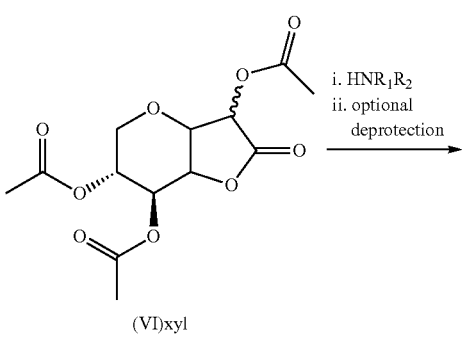

(VI)xyl

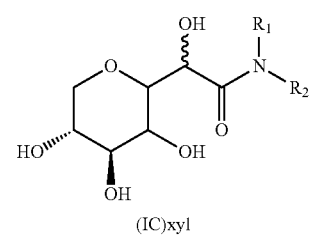

(IC)xyl

In this scheme, the intermediate (IB)xyl or the corresponding acid form obtained after acidification in particular denotes the compound (IB)xylose below:

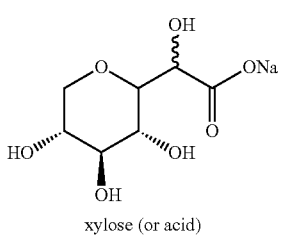

xylose (or acid) (IB)

the compound (VI)xyl in particular denotes the compound (VI)xylose below

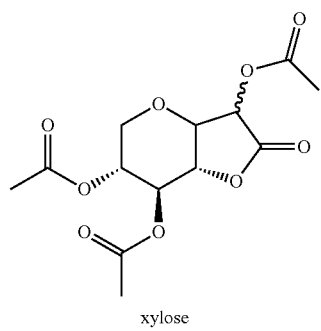

xylose and the compound (IC) in particular denotes the compound (IC)xylose below:

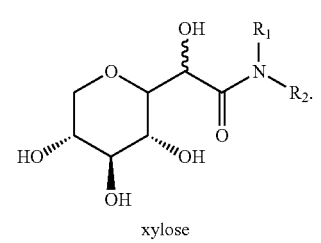

xylose

Similarly, when the saccharide (II) is an L-rhamnose, the scheme for synthesizing the corresponding amides (IC), of formula (IC)rhamn, is as follows:

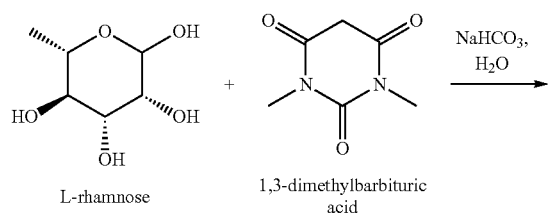

L-rhamnose    1,3-dimethylbarbituric acid

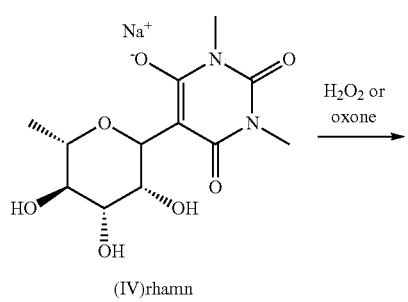

(IV)rhamn

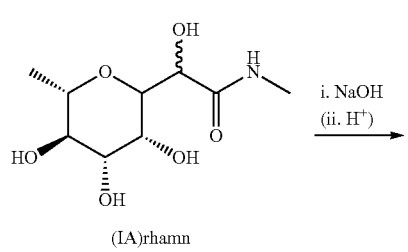

(IA)rhamn

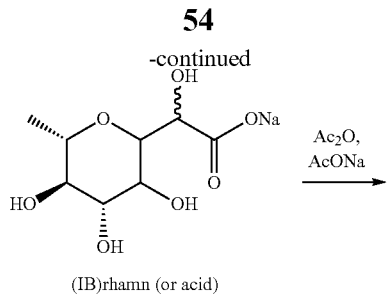

(IB)rhamn (or acid)

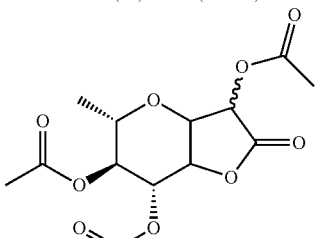

(VI)rhamn

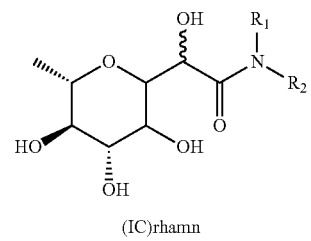

(IC)rhamn

In this scheme, the intermediate (IB)rhamn or the corresponding acid form obtained after acidification in particular denotes the compound (IB)rhamnose below:

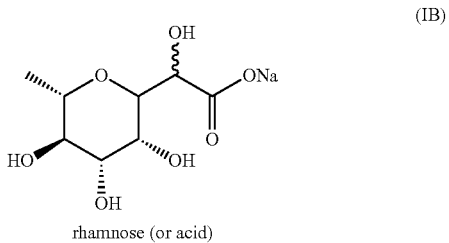

rhamnose (or acid)

the compound (VI)rhamn in particular denotes the compound (VI)rhamnose below

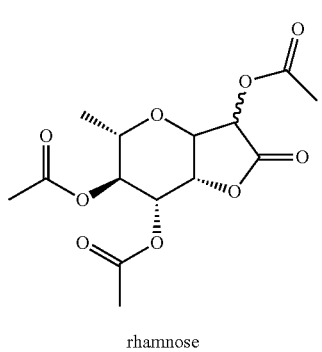

rhamnose and the compound (IC) in particular denotes the compound (IC)rhamnose below:

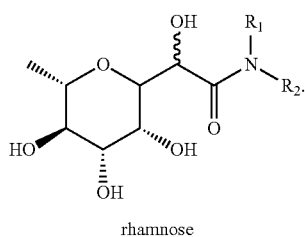
(IC)

rhamnose

When the saccharide (II) is a D-galactose, the scheme for synthesizing the corresponding amides (IC), of formula (ICd)galac, is as follows:

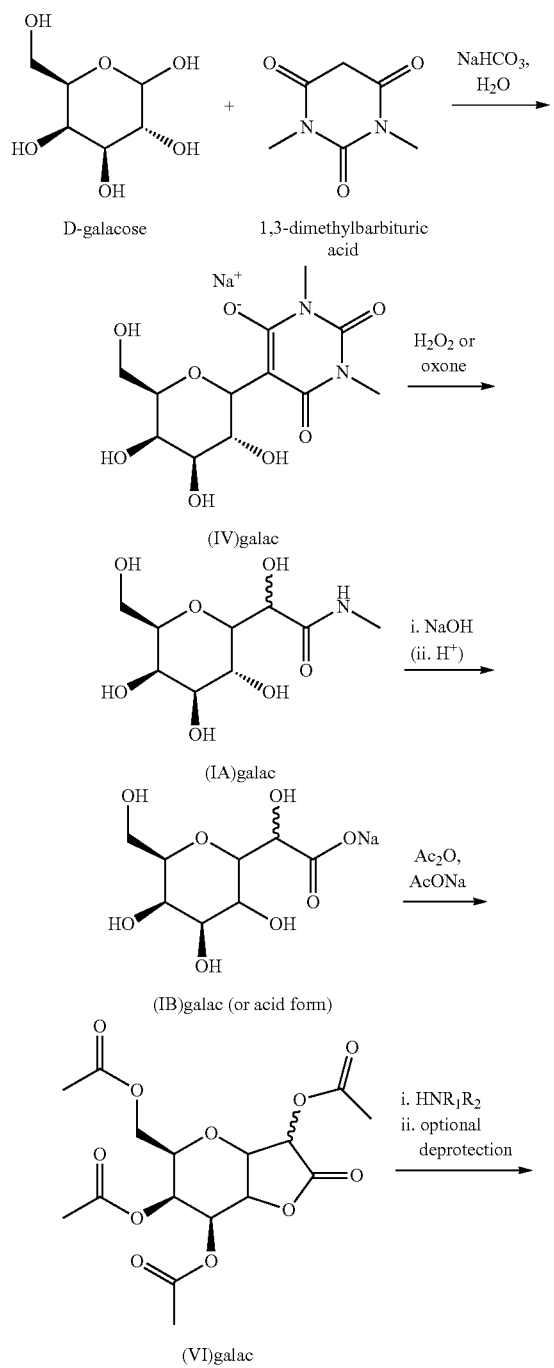

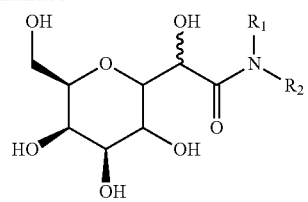
(IC)galac

In this scheme, the intermediate (IB)galac or the corresponding acid form obtained after acidification in particular denotes the compound (IB)galactose below:

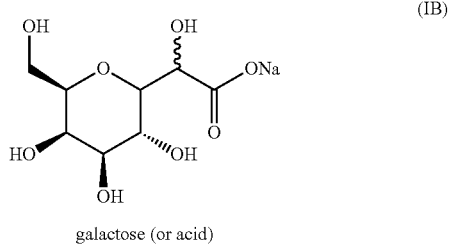

galactose (or acid)

the compound (VI)galac in particular denotes the compound (VI)galactose below

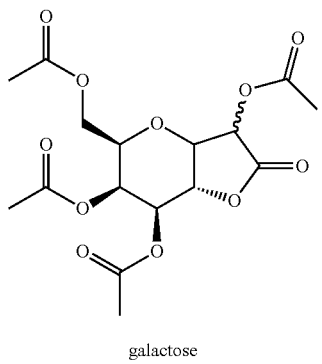

galactose and the compound (IC) in particular denotes the compound (IC)galactose below:

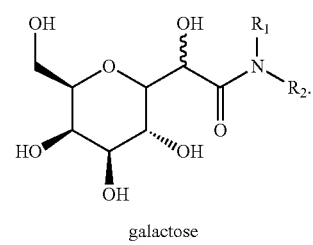

galactose

When the saccharide (II) is a D-mannose, the scheme for synthesizing the corresponding amides (IC), of formula (IC)mann, is as follows:

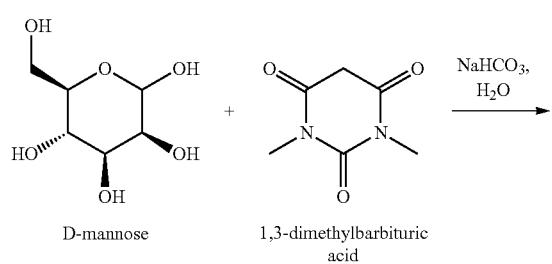

D-mannose + 1,3-dimethylbarbituric acid → (NaHCO₃, H₂O)

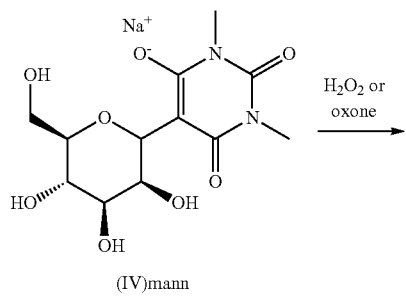

(IV)mann → (H₂O₂ or oxone)

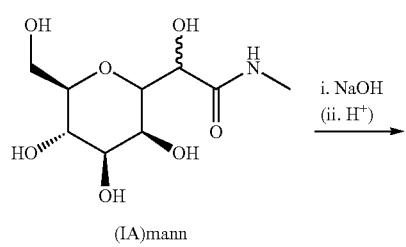

(IA)mann → (i. NaOH, ii. H⁺)

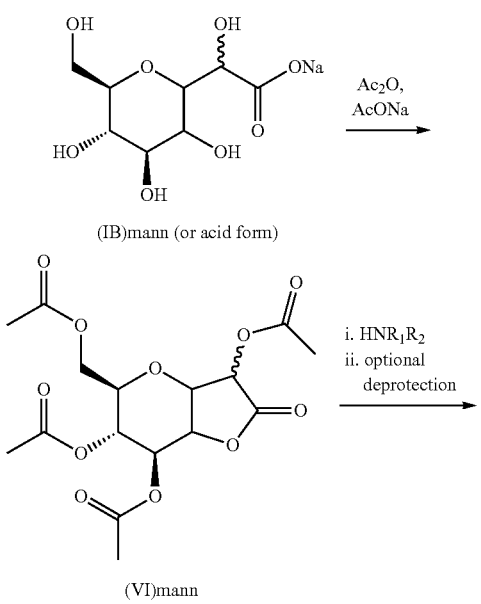

(IB)mann (or acid form) → (Ac₂O, AcONa) → (VI)mann → (i. HNR₁R₂, ii. optional deprotection)

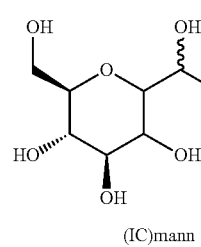

(IC)mann

In this scheme, the intermediate (IB)mann or the corresponding acid form obtained after acidification in particular denotes the compound (IB)mannose below:

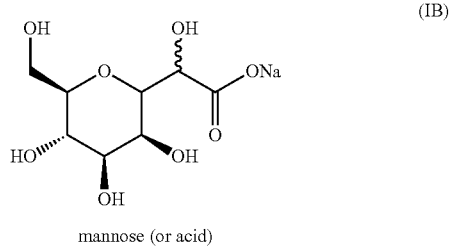

mannose (or acid) (IB)

the compound (VI)mann in particular denotes the compound (VI)mannose below:

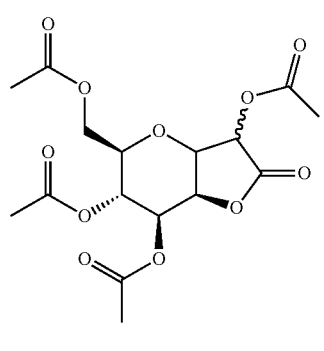

mannose (VI)

and the compound (IC) in particular denotes the compound (IC)mannose below:

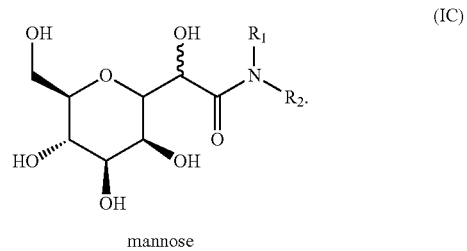

mannose (IC)

Similarly, when the saccharide (II) is a D-lactose, the scheme for synthesizing the corresponding amides, of formula (IC)lact, is as follows:

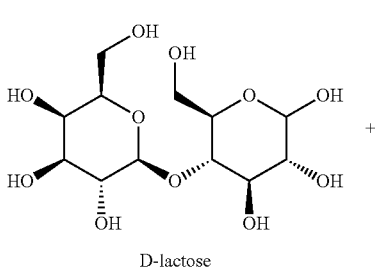

D-lactose +

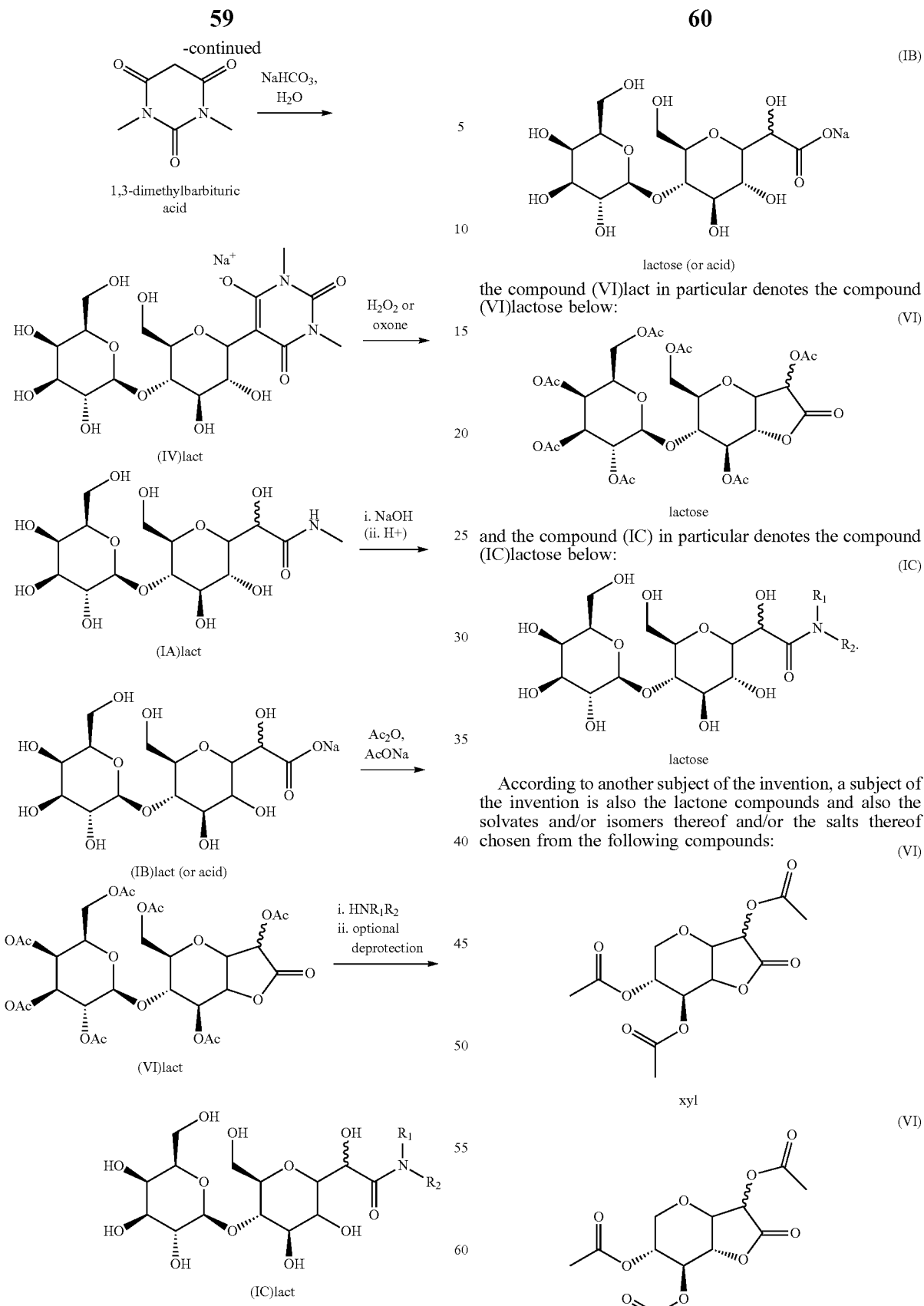

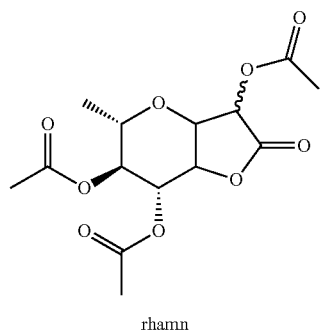

rhamn

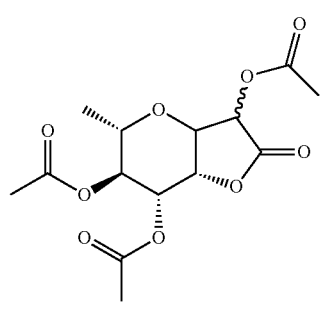

rhamnose

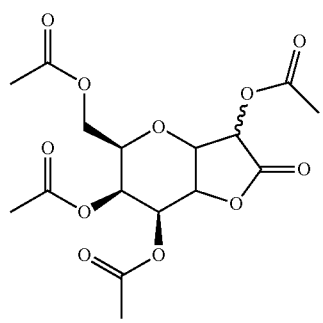

galac

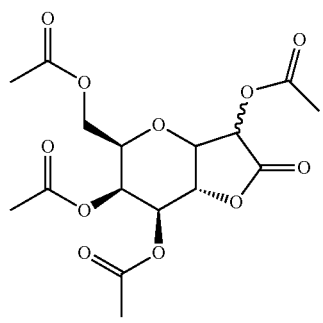

galactose

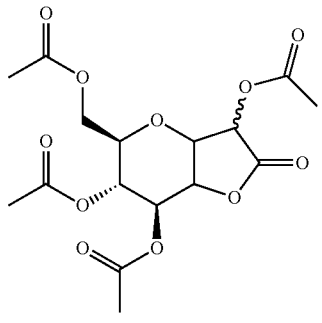

mann

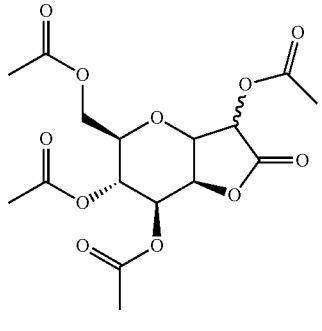

mannose

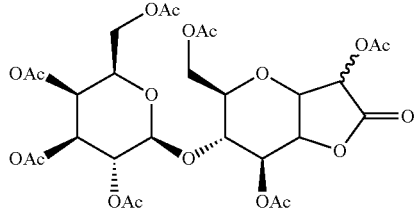

lact

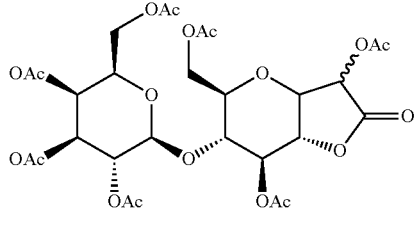

lactose

According to a preferred embodiment, a subject of the invention, a subject of the invention is also the lactone compounds, and also the solvates and/or isomers thereof and/or the salts thereof chosen from the compounds (VI)xyl, (VI)rhamn, (VI)galac, (VI)mann and (VI)lact and in particular the compounds (VI)xylose, (VI)rhamnose, (VI)galactose, (VI)mannose and (VI)lactose, and most particularly the compounds (VI)rhamnose, (VI)galactose, (VI)mannose and/or (VI)lactose, as defined previously.

In the Particular Case of the Compounds of Formulae (Ia¹) and (Ia²):

The compounds of formulae (Ia¹) and (Ia²) can be obtained via the synthetic route below (scheme 2), from the compound (IF), the preparation process of which is described above:

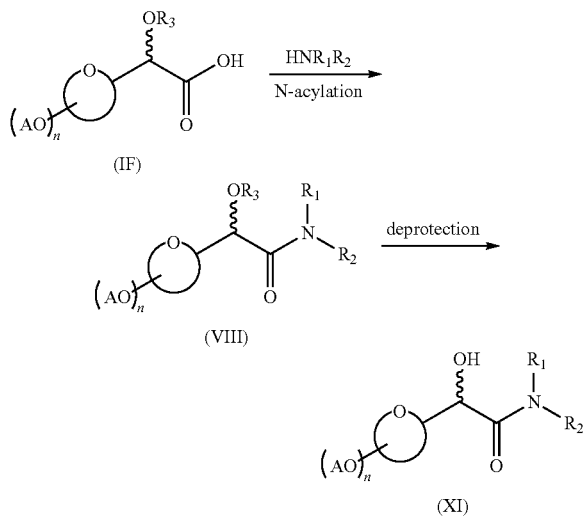

The compound (IF), the hydroxyl groups of which are preferably substituted or protected (groups A and $R_3$), undergoes an N-acylation reaction with an aromatic amine $HNR_1R_2$, so as to obtain a family of compounds (VIII) including the compounds of formula (Ia²).

A step of deprotection of the hydroxyl functions of the sugar unit (groups A) and of the optional other functions present in the groups $R_1$ and/or $R_2$ gives the group of compounds (XI) which include the compounds of formula (Ia¹).

In the Particular Case of the Compounds of Formulae (Ib¹) and (Ib²):

The compounds of formulae (Ib¹) and (Ib²) can be obtained via the synthetic route below (scheme 3), from the compound (VI), the preparation process of which is described above:

Opening of the lactone (VI) is carried out through attack by the compound (X). Two variants are possible:
the use of a single equivalent of the amine (X) preferentially gives the group of compounds (XI), which includes the compounds of formula (Ib²); the reaction is generally carried out in a non-protic polar solvent such as dichloromethane (DCM), THF or DMF, at a temperature of between 20° C. and 150° C., optionally in the presence of a base such as diisopropylethylamine (DIEA) or triethylamine (TEA);
the use of an excess of amine (X), optionally itself as a solvent, can directly give the compound (XII), which includes the compounds of formula (Ib¹), provided that the group $R_3$ can be cleaved by the action of an amine, that is to say the case in particular of the acetyl group.

Depending on the nature of the groups A, $R_3$, $R''_1$, $R''_4$, $R''_5$ and $R''_6$, various deprotection and/or hydrolysis and/or aminolysis reactions, in particular of ester function(s), can make it possible to convert the compounds (XI) into compounds (XII), so as to finally give the compounds of formula (Ib¹).

All the reagents are obtained by conventional methods known by those skilled in the art. The latter will take care to protect or deprotect according to the synthesis steps. For example:

The compounds can be obtained from:
a sugar (II) of scheme 1 comprising OH group(s) which are free or substituted with a $C_1$-$C_6$ alkyl group or with a $C_1$-$C_6$ alkylcarbonyl group, or comprising an OH group protected by a PG that is accessible according to the methods described by Peter G. M. Wuts and Theodora W. Greene, in Greene's Protective Groups in Organic Synthesis, Fourth Edition, Wiley, 2006; processes for alkylation, acylation or protection of the hydroxyls of sugars are known and in particular described in Durantie, Estelle et al, Chemistry—A European Journal, 18(26), 8208-8215 (2012).

The sugar (II) of scheme 1 can also contain one or more amino groups substituted with the same $C_1$-$C_6$ alkylcarbonyl group, or with a PG such as those described by Peter G. M. Wuts and Theodora W. Greene, in Greene's Protective Groups in Organic Synthesis, Fourth Edition, Wiley, 2006. The processes for alkylation, acylation or protection of the

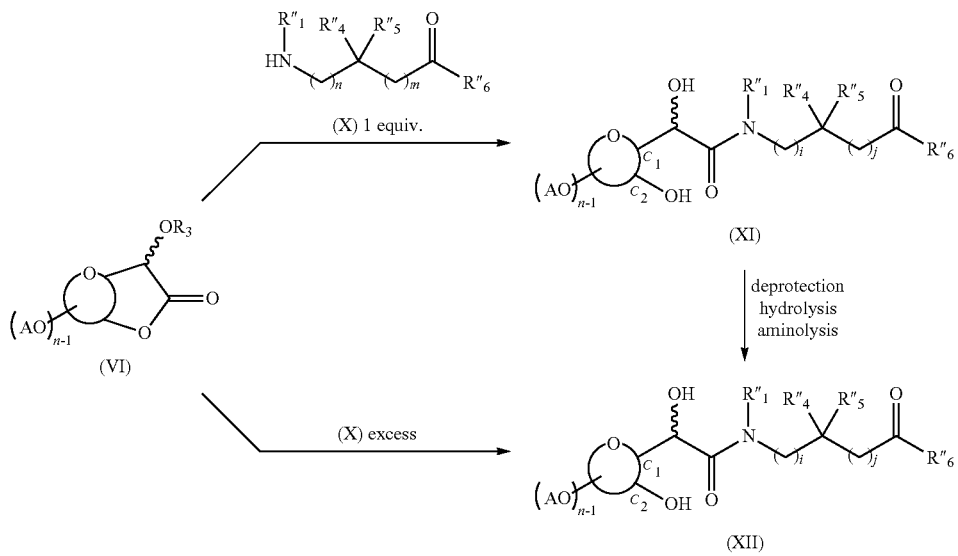

hydroxyls of sugars are known by those skilled in the art and are in particular described in: Durantie, Estelle et al, *Chemistry—A European Journal*, 18(26), 8208-8215 (2012). The N-acylation methods are also well known by those skilled in the art and consist in reacting the amine with either a reactive derivative of a carboxylic acid, such as an acid anhydride or an acid halide (acid chloride), or a carboxylic acid activated in situ via a coupling agent such as HOBt, EDCl, CDl, DCC, HATU or PyBOP, in the optional presence of an organic base such as DIEA or TEA, or of a mineral base such as NaOH, and optionally of DMAP in an equimolar or catalytic amount, in a non-protic polar solvent such as DCM, THF, DMF or acetonitrile, or optionally a protic solvent such as water.

The barbituric acid derivative (III) optionally N-disubstituted with the radicals $R_1$ corresponding to the ($C_1$-$C_{18}$) alkyl, aryl or aryl($C_1$-$C_4$)alkyl groups, the aryl radical being optionally substituted in particular with OMe, OEt, and/or hydroxyl protected with a PG as previously defined; (III) possibly being prepared for example according to the process described by Guoyao Xia et al., *J. Med. Chem.* 2011, 54, 2409-2421.

The hydroxyl group of (IA) in the alpha position with respect to the C=O group can be alkylated or acylated so as to give the compound (IA') in which R' is other than H, and corresponds to the groups ($C_1$-$C_{18}$)alkyl, ($C_2$-$C_{18}$)alkenyl, ($C_1$-$C_{18}$)alkynyl, aryl($C_1$-$C_4$)alkyl, the aryl radical being optionally substituted with a ($C_1$-$C_4$)alkoxy group such as OMe, OEt, and/or hydroxyl optionally protected with a PG (preferably identical to that optionally present on the aryl radical of the group $R_1$), or ($C_1$-$C_{18}$)alkylcarbonyl, or ($C_1$-$C_{18}$)alkenylcarbonyl. R' and/or $R_3$ can also correspond to a hydroxyl-protective group which may be required in the context of subsequent steps. The step for alkylation of the hydroxyl group is generally carried out by treatment with a base, often a relatively strong base, of NaH, tBuOK or tBuONa type, in the presence of an alkylation agent such as an alkyl halide, in a non-protic polar solvent such as DMF, NMP, THF, acetonitrile or acetone. The step for acylation of the hydroxyl group is generally carried out by treatment with either a reactive derivative of a carboxylic acid, such as an acid anhydride or an acid halide (acid chloride), or a carboxylic acid activated in situ via a coupling agent such as HOBt, EDCl, CDl or DCC, optionally in the presence of a base such as pyridine, triethylamine or diisopropylethylamine, sodium acetate or sodium hydroxide, and optionally of DMAP in an equimolar or catalytic amount, in a non-protic polar solvent such as acetonitrile, pyridine, dichloromethane, THF or acetone, or optionally a protic solvent such as water. Alternatively, the hydroxyl can be treated with a carboxylic acid in an acid medium (APTS, anhydrous HCl, $H_2SO_4$), with a device for eliminating the water formed, such as the presence of a desiccant, for instance silica gel, $Na_2SO_4$, $MgSO_4$ or $P_2O_5$, or a Dean Stark apparatus using a volatile solvent which forms an azeotrope with water, for instance toluene or cyclohexane.

If the hydroxyls of the sugar unit (II) and the hydroxyl in the alpha position with respect to C=O are substituted with the same group, then the starting point is directly the reagent (II) comprising a non-protected sugar unit, in order to subsequently carry out the step of acylation or alkylation of all the hydroxyls in one go on the compound (IA).

It is understood that, when it is necessary to protect the hydroxyl and/or amino functions which might react and parasitize the subsequent reaction, said functions are protected according to the processes known by those skilled in the art previously mentioned, then the reaction in question is carried out, then the hydroxyl and/or amine groups are deprotected by the processes known by those skilled in the art, previously mentioned, so as to again render the hydroxyls and/or amines free.

For example, the following reactions can be carried out by protecting, then carrying out the desired reaction, then deprotecting:

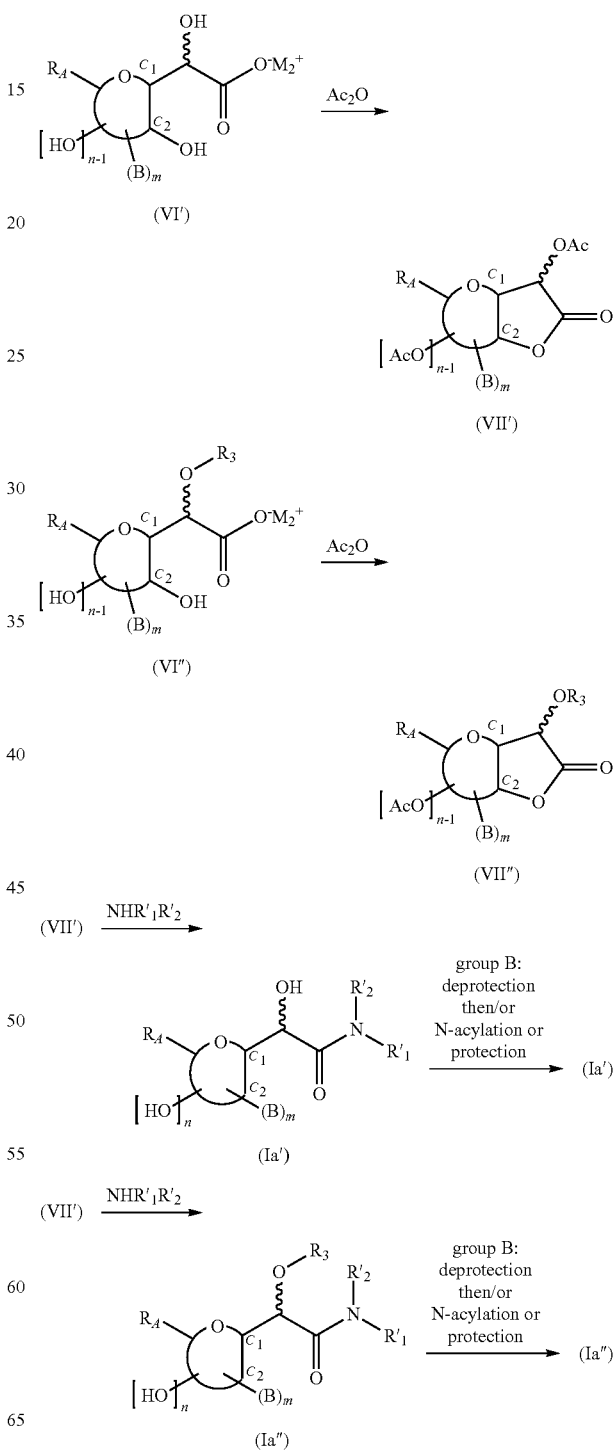

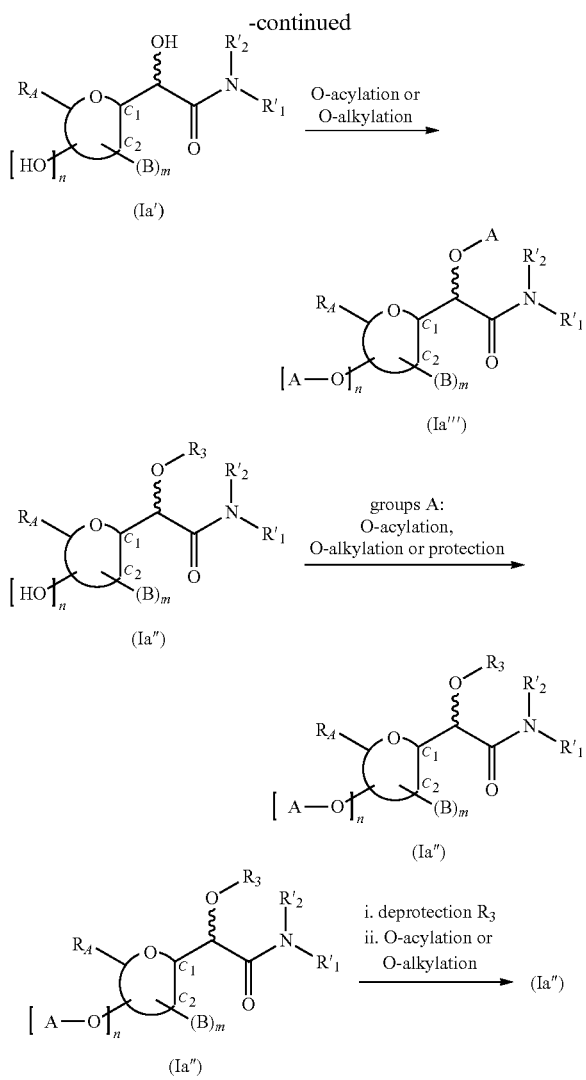

in which schemes B denotes an amino radical $NR_bR_c$ as previously defined; $R'_1$, respectively $R'_2$, denotes an $R_1$, respectively $R_2$, group substituted with a protective group, $R_1$ and $R_2$ having the same definitions as previously given.

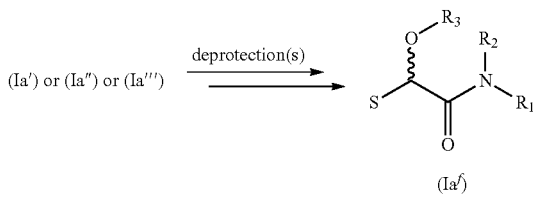

As compounds of formula (I), use may be made of the compounds 1 to 21 previously described.

The compounds of formula (I) according to the invention find a most particular application in the cosmetic field.

A subject of the invention is also a composition containing at least one compound of formula (I), and preferably at least one compound of formula (Ia$^1$), (Ia$^2$), (IBB), (Ib$^1$), (Ib$^2$) and/or (Ic) defined above, and more particularly at least one compound 1 to 21 as defined previously.

The composition according to the invention is advantageously a cosmetic composition. The composition according to the invention is advantageously a composition intended for topical application.

The composition according to the invention advantageously comprises, in a physiologically acceptable medium, at least one compound of formula (I) as described previously, and preferably at least one compound of formula (Ia$^1$), (Ia$^2$), (IBB), (Ib$^1$), (Ib$^2$) and/or (Ic) defined above, and more particularly at least one compound 1 to 21 as defined previously.

The term "physiologically acceptable medium" means a medium that is compatible with human keratin materials such as bodily or facial skin, lips, mucous membranes, eyelashes, nails, the scalp and/or head hair.

The compound of formula (I), and especially the compound of formula (Ia$^1$), (Ia$^2$), (IBB), (Ib$^1$), (Ib$^2$) and/or (Ic), or alternatively 1 to 21 defined above (each compound of formula (I) and especially each compound of formula (Ia$^1$), (Ia$^2$), (IBB), (Ib$^1$), (Ib$^2$) and/or (Ic) and more particularly a compound 1 to 21 if the composition comprises several thereof) may be present in the composition according to the invention in an amount which may be between 0.01% and 10% by weight, preferably between 0.1% to 5% by weight, especially between 0.5% to 3% by weight, relative to the total weight of the composition.

The composition according to the invention is advantageously a cosmetic composition: it may comprise adjuvants usually used in the cosmetic field. The composition may be an aqueous composition, i.e. a composition containing water or a mixture of water and of water-miscible solvents such as C2-C6 alcohols.

Mention may be made especially of: organic solvents, especially C2-C6 alcohols; oils, especially hydrocarbon-based oils, silicone oils; waxes, pigments, fillers, dyes, surfactants, emulsifiers; cosmetic active agents, polymers, thickeners, preserving agents, fragrances, bactericides, odour absorbers, antioxidants.

According to one advantageous form of the invention, the cosmetic composition contains at least one compound of formula (I), and in particular at least one compound of formulae (Ia$^1$), (Ia$^2$), (IBB), (Ib$^1$), (Ib$^2$) and/or (Ic), as previously defined, and at least one additive chosen from fragrances, oils, waxes, surfactants, thickeners, dyes, bactericides and preservatives.

In a preferred mode, the cosmetic composition according to the invention contains at least one compound chosen from the compounds 1 to 21 previously defined, and also the solvates thereof such as hydrates, and the organic or mineral acid or base salts thereof.

These optional cosmetic adjuvants may be present in the composition in a proportion of from 0.001% to 80% by weight, especially 0.1% to 40% by weight, relative to the total weight of the composition. In any event, these adjuvants, and also the proportions thereof, will be chosen by a person skilled in the art such that the advantageous properties of the compounds according to the invention are not, or are not substantially, adversely affected by the envisaged addition.

As active agents, it will be advantageous to introduce into the composition according to the invention at least one compound chosen from: desquamating agents; calmatives, organic or inorganic photoprotective agents, moisturizers; depigmenting agents other than those that are the subject of the present invention; antiglycation agents; NO-synthase inhibitors; agents for stimulating the synthesis of dermal or epidermal macromolecules and/or for preventing their degradation; agents for stimulating the proliferation of fibroblasts and/or keratinocytes or for stimulating keratinocyte differentiation; dermo-decontracting agents; tensioning agents; antipollution agents and/or free-radical scavengers; agents acting on the microcirculation; ceramides; agents acting on the energy metabolism of cells; and mixtures thereof.

The composition according to the invention may in particular be in any presentation form normally used in the cosmetic field, and especially in the form of an optionally gelled aqueous or aqueous-alcoholic solution, a dispersion of the lotion type, which may be a two-phase dispersion, an oil-in-water or water-in-oil or multiple emulsion (for example W/O/W or O/W/O), an aqueous gel, a dispersion of oil in an aqueous phase with the aid of spherules, these spherules possibly being polymer nanoparticles such as nanospheres and nanocapsules or, better still, lipid vesicles of ionic and/or nonionic type; aqueous or oily gel. These compositions are prepared according to the usual methods. The composition according to the invention may constitute a skincare composition, and especially a cream for cleansing, protecting, treating or caring for the face, the hands, the feet, the major anatomical folds or the body (for example day creams, night creams, makeup-removing creams, foundation creams, antisun creams); a fluid foundation, a makeup-removing milk, a protective or care body milk, an antisun milk; a skincare lotion, gel or foam, for instance a cleansing lotion.

A subject of the invention is also a process for cosmetic treatment of the skin, comprising the application, to the skin, of a composition comprising at least one compound of formula (I), and preferably at least one compound of formula (Ia$^1$), (Ia$^2$), (IBB), (Ib$^1$), (Ib$^2$) and/or (Ic) defined above, and more particularly at least one compound 1 to 21, as previously defined.

In another particular embodiment, the treatment process aims to prevent the signs of skin ageing.

Preferably, the treatment process aims to treat the signs of skin ageing.

In a particular embodiment, the invention also relates to a process for cosmetic treatment of the skin, intended for preventing and/or treating ageing, comprising a step consisting in applying, to skin exhibiting signs of skin ageing, a composition comprising at least one compound of formula (I), and in particular at least one compound (Ia$^1$), (Ia$^2$), (IBB), (Ib$^1$), (Ib$^2$) and/or (Ic) defined above, and more particularly at least one compound 1 to 21, as previously defined.

In particular, the process according to the invention aims to improve the radiance and/or the uniformity of the complexion; to improve the radiance and/or the transparency of the skin; to improve the softness, the suppleness and/or the elasticity of the skin and/or the tonicity of the skin and/or the firmness of the skin; and/or to prevent and/or reduce wrinkles and/or fine lines.

In particular, the cosmetic treatment process aims to maintain and/or stimulate the moisturization and/or combat the drying out of keratin materials, in particular the skin.

The invention also relates to a process for cosmetic treatment of keratin materials, such as the skin, intended for preventing and/or treating the signs of dryness of said materials, in particular dryness of the skin, comprising a step consisting in applying, to said materials such as the skin and preferably to skin exhibiting signs of dryness, a composition comprising at least one compound of formula (I), and in particular at least one compound (Ia$^1$), (Ia$^2$), (IBB), (Ib$^1$), (Ib$^2$) and/or (Ic) defined above, and at least particularly at least one compound 1 to 21, as previously defined.

In a particular embodiment, the compounds of formula (I), and in particular the compounds (Ia$^1$), (Ia$^2$), (IBB), (Ib$^1$), (Ib$^2$) and/or (Ic) defined above, are in particular useful as agents for combating the signs of ageing, in particular chronobiological ageing, of the skin.

The present invention also relates to the use of at least one compound of formula (I), and in particular the compounds (Ia$^1$), (Ia$^2$), (IBB), (Ib$^1$), (Ib$^2$) and/or (Ic) defined above, a salt thereof, or a solvate thereof, for preparing a composition intended for combating the signs of ageing, in particular chronobiological ageing, of the skin. It also relates to the use of of at least one compound of formula (I) as defined above, in a cosmetic composition comprising a physiologically acceptable medium, as an agent intended for combating the signs of skin ageing, and/or as a moisturizer.

In a particular embodiment, the present invention also relates to the use of a compound or of a composition according to the invention for combating the signs of ageing, in particular chronobiological ageing, of the skin, for improving moisturization of the skin. The compounds or compositions according to the invention are in particular intended for the correction of all skin re-epithelialization disorders.

In a particular embodiment, the compounds or compositions according to the invention are particularly suitable for combating the signs of chronobiological ageing of the epidermis. During chronobiological ageing, the thickness of the epidermis becomes reduced, the cell divisions decreasing in number. By facilitating cell multiplication, in particular epidermal cell multiplication, the regeneration of the epidermis is facilitated and the skin has a younger appearance.

The compounds or compositions according to the invention are in particular intended for preventing or reducing wrinkles and fine lines, and/or thinning of the skin and/or the flaccid and/or withered skin appearance. The present invention thus also relates to the use of at least one compound according to the invention in a cosmetic composition for preventing or reducing wrinkles and fine lines, and/or thinning of the skin and/or the flaccid and/or withered skin appearance.

The composition also comprises a physiologically acceptable medium, which is preferentially a cosmetically or pharmaceutically acceptable medium, in particular a dermatologically acceptable medium, i.e. a medium that has no odour, colour or appearance that is unpleasant to the user. In particular, the composition is suitable for topical application to the skin and skin integuments.

The term "physiologically acceptable medium" is intended to mean a medium that is compatible with human skin and skin integuments.

The composition according to the invention may comprise any adjuvant commonly used in the envisaged application field.

Mention may be made in particular of water; organic solvents, in particular $C_1$-$C_6$ alcohols and $C_2$-$C_{10}$ carboxylic acid esters; carbon-based and/or silicone oils, of mineral, animal and/or plant origin; waxes, pigments, fillers, dyes, surfactants, emulsifiers, coemulsifiers; cosmetic or dermatological active agents other than the compounds of the invention, UV-screening agents, polymers, hydrophilic or lipophilic gelling agents, thickeners, preservatives, fragrances, bactericides, odour absorbers and antioxidants. These optional adjuvants may be present in the composition in a proportion of from 0.001% to 80% by weight and in particular from 0.1% to 40% by weight relative to the total weight of the composition.

The composition according to the invention may constitute a makeup composition, or preferentially a skincare or skin moisturization composition, and in particular a cleansing, protecting, treating or care cream for the face, the hands, the feet, the major anatomical folds or the body (for example day creams, night creams, makeup-removing creams, foundation creams or anti-sun creams); a fluid foundation, a makeup-removing milk, a protective or care body milk or an anti-sun milk; a skincare lotion, gel or mousse, such as a cleansing lotion, or a hair composition.

The composition according to the invention is, in a particular embodiment, an anti-ageing, in particular care, composition intended for treating and/or combating, cosmetically, the external signs of skin ageing; the composition is more particularly a care composition for mature skin.

The composition according to the invention may be a moisturizing composition, in particular care composition, intended for treating and/or combating, cosmetically, the external signs of dryness of the skin; the composition is more particularly a moisturizing composition for dry skin.

A subject of the invention is also a non-therapeutic cosmetic process for depigmenting, lightening and/or bleaching keratin materials, especially the skin, comprising the application of the cosmetic composition described previously comprising at least one compound of formula (I) and preferably at least one compound of formula (Ia$^1$), (Ia$^2$), (IBB), (Ib$^1$), (Ib$^2$) and/or (Ic) defined above, and more particularly at least one compound 1 to 21 as defined previously, as defined previously.

Preferably, it is a process for depigmenting, lightening and/or bleaching the skin.

The invention also relates to the non-therapeutic cosmetic use of at least one compound of formula (I) as defined previously, and preferably at least one compound of formula (Ia$^1$), (Ia$^2$), (IBB), (Ib$^1$), (Ib$^2$) and/or (Ic) defined above, and more particularly at least one compound 1 to 21 as defined previously, as an agent for bleaching, lightening and/or depigmenting keratin materials, especially the skin.

The various examples below describe various synthetic routes for obtaining the compounds of formula (I).

In these schemes, "r.t." means room temperature.

The invention is illustrated in greater detail by the following non-limiting examples.

EXAMPLES

Example 1

Synthesis of Compounds 1, 2 and 3

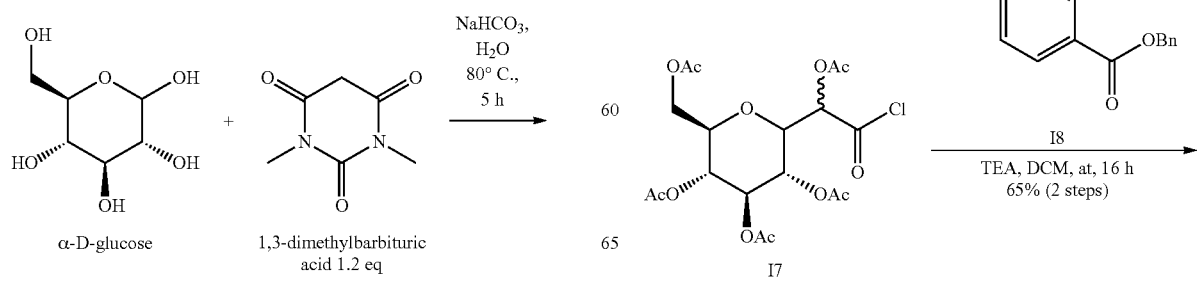

-continued

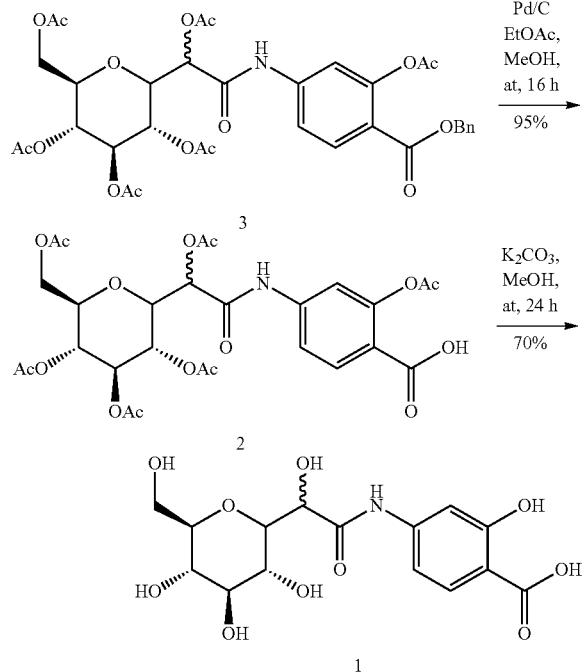

D-glucose (5 g), dissolved in water (56 ml), is introduced into a 250 ml single-necked round-bottomed flask. 1,3-Dimethylbarbituric acid (4.33 g) is added with stirring, then $NaHCO_3$ is added up to pH 7. After neutralization, the round-bottomed flask is equipped with a condenser and the mixture is heated at 80° C. for 5 h. The reaction is monitored by TLC in 1:1 dichloromethane (DCM)/MeOH. The reaction mixture is concentrated under vacuum. The residue obtained is taken up in water, then precipitated from acetone and filtered and the solid I1 obtained is dried under vacuum. It is isolated in the form of an orange powder (9.3 g, yield 98%). The $^1H$ NMR spectra and the mass spectrometry are in accordance with the expected structure.

5 g of product I1 are dissolved in 10 ml of water at ambient temperature, then 30% $H_2O_2$ (3 ml) is added. The reaction mixture is stirred at ambient temperature for 2 hours. 0.21 equiv. of an aqueous 20% sodium metabisulfite solution is then added, and stirring is continued for 1 h at ambient temperature. The absence of peroxide is verified, then the reaction mixture is poured into 300 ml of ethanol. The precipitate formed is filtered off, and the filtrate is concentrated to a minimum volume. A further precipitate forms, and is collected and dried under vacuum at 30° C. (first product fraction, 1.6 g). The filtrate is again taken up in ethanol, the precipitate formed is filtered off, and the filtrate is concentrated to dryness to give another product fraction (0.8 g). Two batches of product I2 are thus recovered in the form of a white solid (2.4 g, yield 65%). The $^1H/^{13}C$ NMR spectra and the mass spectrometry are in accordance with the expected structure.

Compound I2 (2.56 g, 10 mmol) was added to a solution of NaOH (4 g, 100 mmol) in 50 ml of water. After stirring at 100° C. for 5 h, the reaction mixture is cooled to ambient temperature and then adjusted to pH 4 by adding an ion exchange resin. The resin is then removed by filtration. The filtrate is concentrated to give 2.3 g of the acid salt I3 in the form of a grey solid (quantitative yield). The $^1H$ NMR spectra and the mass spectrometry are in accordance with the expected structure.

A mixture of the salt I3 (3.3 g, 12.6 mmol), benzyl bromide (2.6 g, 15.2 mmol), 12.6 ml of n-$Bu_4NF$ in 1 M solution in THF, and 20 ml of DMF, is stirred at ambient temperature for 16 h. The mixture is then concentrated to dryness. The residue is purified by silica column chromatography (dichloromethane/methanol=10/1) to give 2.4 g of the benzyl ester I4 in the form of a white solid (yield 58%). The $^1H$ NMR spectra and the mass spectrometry are in accordance with the expected structure.

Acetic anhydride (19.6 g, 192 mmol) and pyridine (7.6 g, 96 mmol) are added to a solution of compound I4 (6.3 g, 19.2 mmol) in dichloromethane (30 ml). The reaction mixture is stirred for 16 h at ambient temperature, then the acetic anhydride is evaporated off and 50 ml of water are added. The mixture is extracted 3 times with dichloromethane. The organic phases are combined, washed with a saturated aqueous $NaHCO_3$ solution, dried over $Na_2SO_4$, filtered and evaporated. The residue is purified by silica gel chromatography (ethyl acetate/petroleum ether 1:2) to give compound I5 (white viscous solid, 2 g, yield=21% over the 5 steps at the start of the D-glucose).

Pd/C 10% (0.2 g) is added to a solution of compound I5 (2 g, 3.7 mmol) in a 1:1 methanol/ethyl acetate mixture (20 ml). The mixture is hydrogenated under a hydrogen atmosphere for 16 h at ambient temperature. After filtration, the filtrate is evaporated to dryness to give compound I6 (white solid, 1.5 g, yield=90%).

Oxalyl chloride (0.68 g, 5.4 mmol) and a drop of DMF are added to a solution of compound I6 (2 g, 4.5 mmol) in dichloromethane (10 ml). The reaction mixture is stirred for 2 h at ambient temperature and then evaporated to dryness. The residue I7 obtained is used directly in the next step.

Triethylamine (0.9 g, 8.9 mmol) was added to a solution of compound I8 ([1444836-72-9], 1.27 g, 4.5 mmol) in dichloromethane (10 ml), then a solution of the crude residue I7 (2.08 g, 4.5 mmol) in dichloromethane (10 ml) was added dropwise. At the end of the addition, the reaction mixture was stirred for 16 h at ambient temperature, and then evaporated to dryness. The residue obtained was purified by silica gel chromatography (ethyl acetate/petroleum ether 1:2) to give compound 3 (white solid, 2 g, yield=65% over 2 steps).

Pd/C 10% (0.2 g) is added to a solution of compound 3 (2 g, 2.8 mmol) in a 2:1 methanol/ethyl acetate mixture (15 ml). The mixture is hydrogenated under a hydrogen atmosphere for 16 h at ambient temperature. After filtration, the filtrate is evaporated to dryness to give compound 2 (white solid, 1.66 g, yield=95%).

$K_2CO_3$ (0.733 g, 5.3 mmol) is added to a solution of compound 2 (1.66 g, 2.7 mmol) in methanol (10 ml). The reaction mixture is stirred for 24 h at ambient temperature, then Amberlite IR-120 resin is added. The suspension is stirred for 1 hour at ambient temperature. After filtration, the filtrate is evaporated to dryness. A precipitate forms after addition of 10 ml of ethyl acetate. The solid is filtered off, washed with ethyl acetate and dried under vacuum to give compound 1 (white solid, 0.69 g, yield=70%). The $^1H/^{13}C$ NMR spectra and the mass spectrometry are in accordance with the expected structure.

The MS and NMR spectra are in accordance with the desired product.

Synthesis of Compounds 4 to 21
Synthesis of Compounds 14 and 4

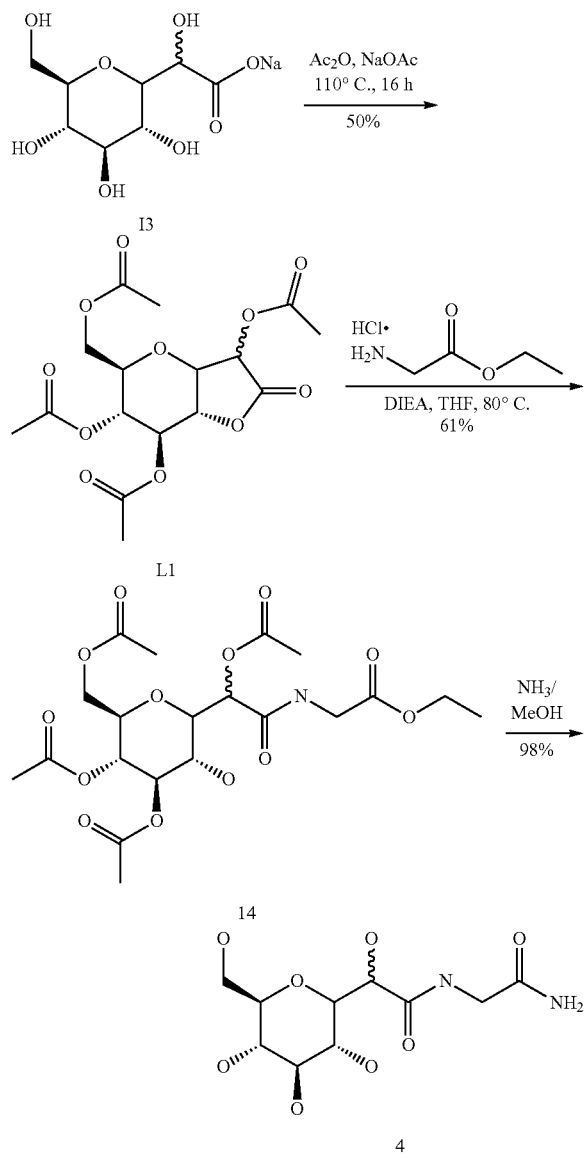

A mixture of the acid salt I3 (2.5 g, 10 mmol), NaOAc (2 g, 10 mmol), and 20 ml of Ac₂O is stirred at 110° C. for 16 h, then the mixture is concentrated to dryness. The residue is taken up in 200 ml of sat. aq. NaHCO₃ and extracted 3 times with ethyl acetate. The organic phases are combined and concentrated under vacuum, and the residue obtained is purified by silica chromatography (petroleum ether/ethyl acetate=2/1) to give 1.9 g of the lactone intermediate L1 in the form of a white solid, yield 50%. The ¹H NMR spectra and the mass spectrometry are in accordance with the expected structure.

A solution of lactone L1 (1.50 g, 3.86 mmol), L-glycine ethyl ester hydrochloride (0.54 g, 3.86 mmol) and DIEA (1.50 g, 11.59 mmol) in THF (50 ml) is stirred for 14 h at 80° C. After the solvent has been evaporated off, 5 ml of ethyl acetate are added in order to dissolve the residue. The organic phase is washed twice with 0.1 M aq. HCl. The aqueous phase is extracted with ethyl acetate. The organic phases are combined, dried over MgSO₄, filtered and evaporated. The residue is purified by silica gel chromatography (ethyl acetate/n-heptane 2:1) to give 14 (beige solid, 1.15 g, yield=61%). The ¹H/¹³C NMR spectra and the mass spectrometry are in accordance with the expected structure.

The product 14 (569 mg, 1.16 mmol) is dissolved in a 7 M solution of aqueous ammonia in methanol (15 ml). The reaction mixture is stirred for 17 hours at ambient temperature. After the solvent has been evaporated off, 5 ml of methyl are added in order to dissolve the residue. A precipitate forms after the addition of 50 ml of ethyl acetate. The solid is filtered off, washed with ethyl acetate and n-heptane, and dried under vacuum to give compound 4 (white solid, 333 mg, yield=98%). The ¹H/¹³C NMR spectra and the mass spectrometry are in accordance with the expected structure.

Synthesis of Compounds 15 and 5

Compound 15 is obtained according to the procedure described for compound 14, from lactone L1 (1.80 g, 4.64 mmol), L-serine ethyl ester hydrochloride (0.79 g, 4.64 mmol) and DIEA (1.80 g, 13.91 mmol). Compound 15 is in the form of a beige solid (1.47 g, yield=61%). The ¹H/¹³C NMR spectra and the mass spectrometry are in accordance with the expected structure.

Compound 5 is obtained according to the procedure described for compound 4, from 15 (1.47 g, 2.82 mmol). Compound 5 is in the form of a beige solid (857 mg, 94%). The ¹H/¹³C NMR spectra and the mass spectrometry are in accordance with the expected structure.

Synthesis of Compounds 16 and 6

Compound 16 is obtained according to the procedure described for compound 14, from lactone L1 (1.0 g, 2.58 mmol), L-proline ethyl ester (0.37 g, 2.58 mmol) and DIEA (3.33 g, 25.75 mmol). It is in the form of a yellow solid (640 mg, yield=49%). The ¹H/¹³C NMR spectra and the mass spectrometry are in accordance with the expected structure.

Compound 6 is obtained according to the procedure described for compound 4, from 16 (640 mg, 1.20 mmol). Compound 6 is in the form of a beige solid (291 mg, yield=72%). The ¹H/¹³C NMR spectra and the mass spectrometry are in accordance with the expected structure.

Synthesis of Compounds 17 and 7

Compound 17 is obtained according to the procedure described for compound 14, from lactone L1 (1.50 g, 3.86 mmol), 1-alanine ethyl ester hydrochloride (0.68 g, 3.86 mmol) and DIEA (1.50 g, 11.59 mmol). It is in the form of a yellow solid (794 mg, yield=35%). The ¹H/¹³C NMR spectra and the mass spectrometry are in accordance with the expected structure.

Compound 7 is obtained according to the procedure described for compound 4, from 17 (794 mg, 1.57 mmol). It is in the form of a beige solid (243 mg, yield=50%). The ¹H/¹³C NMR spectra and the mass spectrometry are in accordance with the expected structure.

Synthesis of compound 18

Compound 18 is obtained according to the procedure described for compound 14, from lactone L1 (1.0 g, 2.58 mmol), L-sarcosine ethyl ester (0.39 g, 2.58 mmol) and DIEA (3.33 g, 25.75 mmol). Yellow solid (650 mg, 50%). The ¹H/¹³C NMR spectra and the mass spectrometry are in accordance with the expected structure.

Synthesis of Compound 9

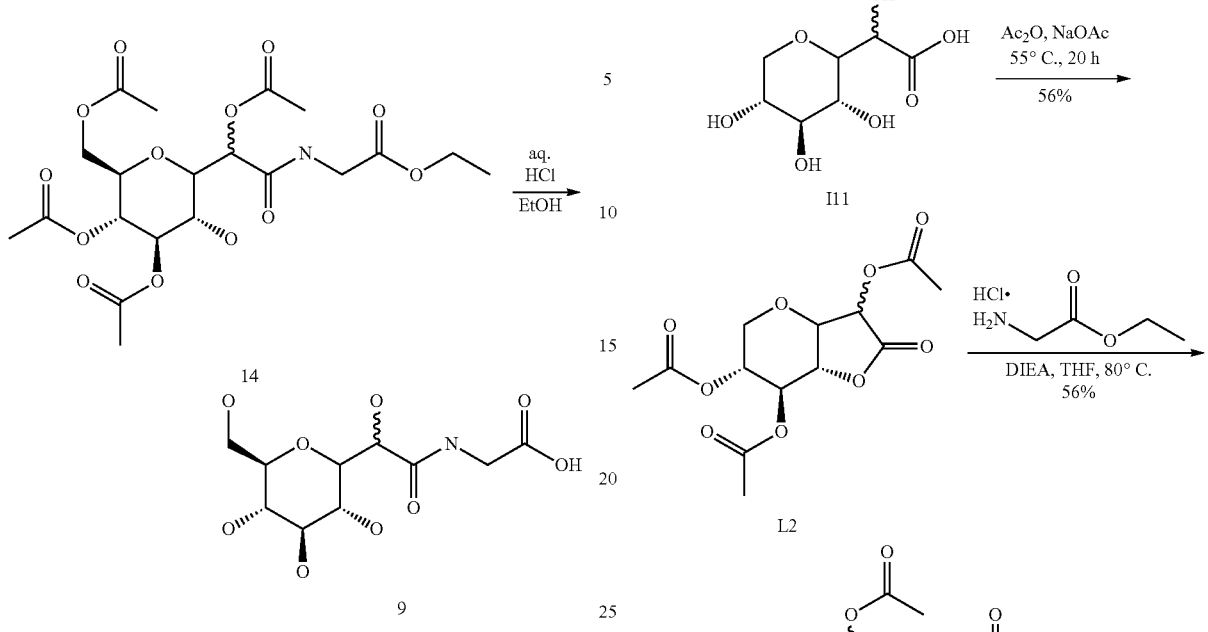

10 drops of conc. HCl are added to a solution of compound 14 (50 mg, 0.10 mmol) in ethanol (5 ml). After stirring for 17 h at ambient temperature, the mixture is evaporated to dryness to give compound 9 (colourless solid, 45 mg, quantitative yield). The ¹H NMR spectra and the mass spectrometry are in accordance with the expected structure.

Synthesis of Compounds 19 and 10

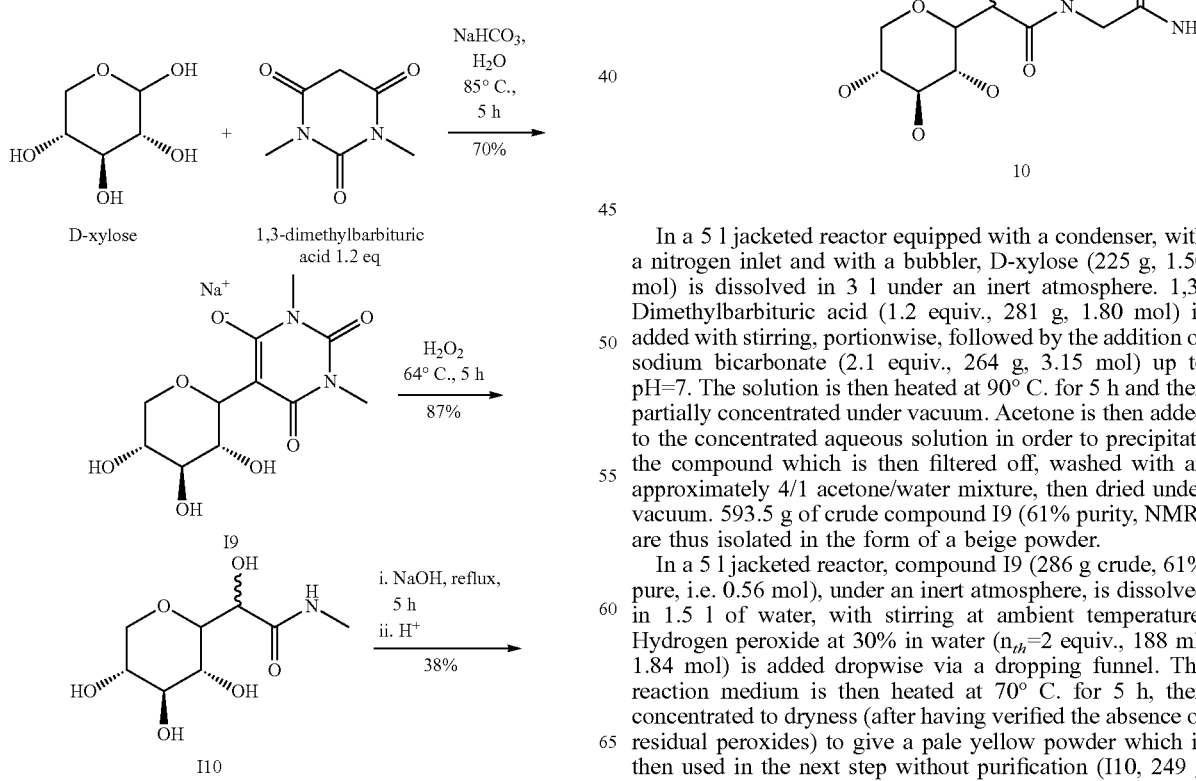

In a 5 l jacketed reactor equipped with a condenser, with a nitrogen inlet and with a bubbler, D-xylose (225 g, 1.50 mol) is dissolved in 3 l under an inert atmosphere. 1,3-Dimethylbarbituric acid (1.2 equiv., 281 g, 1.80 mol) is added with stirring, portionwise, followed by the addition of sodium bicarbonate (2.1 equiv., 264 g, 3.15 mol) up to pH=7. The solution is then heated at 90° C. for 5 h and then partially concentrated under vacuum. Acetone is then added to the concentrated aqueous solution in order to precipitate the compound which is then filtered off, washed with an approximately 4/1 acetone/water mixture, then dried under vacuum. 593.5 g of crude compound I9 (61% purity, NMR) are thus isolated in the form of a beige powder.

In a 5 l jacketed reactor, compound I9 (286 g crude, 61% pure, i.e. 0.56 mol), under an inert atmosphere, is dissolved in 1.5 l of water, with stirring at ambient temperature. Hydrogen peroxide at 30% in water ($n_{th}$=2 equiv., 188 ml, 1.84 mol) is added dropwise via a dropping funnel. The reaction medium is then heated at 70° C. for 5 h, then concentrated to dryness (after having verified the absence of residual peroxides) to give a pale yellow powder which is then used in the next step without purification (I10, 249 g crude, 43% purity, NMR).

In a 5 l jacketed reactor, compound I10 (159.5 g crude, 43% pure, i.e. 0.32 mol), under an inert atmosphere, is dissolved in 2.5 l of water, with mechanical stirring at 20° C. 1 M sodium hydroxide (225 ml, 2.26 mol) is added via a dropping funnel. The reaction medium is then heated at 90° C. for 5 h. The reaction medium (2.7 l) containing the carboxylate of I11 (285 g, 26% purity, NMR) is then purified.

The previous reaction medium (26% purity, NMR, corresponding to 49.0 g of product in acid form I11) is acidified. Compound I11 is then bound to a basic resin and the impurities are eliminated by aqueous washing. Compound I11 is then freed from the basic resin using 0.5 M hydrochloric acid. After lyophilization, a beige powder was obtained (21.45 g, compound I11 at 84% purity, NMR, 38% yield).

A mixture of the acid I11 (8.5 g, 38 mmol), NaOAc (3.2 g, 38 mmol) and 73 ml of Ac$_2$O is stirred at 55° C. for 20 h, then the mixture is treated with diisopropyl ether so as to recover a white solid after filtration. This solid is treated by fractional precipitation from ethyl acetate so as to obtain various fractions of a single diastereoisomer of the lactone L2, denoted dia1. The filtrates are concentrated and purified by silica chromatography (n-heptane/ethyl acetate 8:2) to give 2 other fractions of lactone L2 in the form of mixtures enriched with dia1 or with dia2 (2nd diastereoisomer). In total, 6.11 g of lactone are obtained (white powder, 56% yield). The $^1$H/$^{13}$C NMR spectra and the mass spectrometry are in accordance with the expected structure.

Compound 19 is obtained according to the procedure described for compound 14, from lactone L2 (1.5 g, 4.7 mmol), L-glycine ethyl ester hydrochloride (662 mg, 4.7 mmol) and DIEA (2.5 ml, 14 mmol): Yellow oil, 1.07 g, Yield=56%. The $^1$H/$^{13}$C NMR spectra and the mass spectrometry are in accordance with the expected structure. Compound 10 is obtained according to the procedure described for compound 4, from 19 (800 mg, 1.9 mmol). The ethyl acetate is replaced with acetone for the precipitation. It is isolated in the form of a white powder, 435 mg, yield=86%.

Synthesis of Compounds 20-Dia1 and 11-Dia1

Compound 20-dia1 is obtained according to the procedure described for compound 19, from lactone L2-dia1 (1.34 g, 4.2 mmol), L-serine ethyl ester hydrochloride (719 mg, 4.24 mmol) and DIEA (3.7 ml, 21 mmol). Yellow oil (1 g, 45%). The $^1$H/$^{13}$C NMR spectra and the mass spectrometry are in accordance with the expected structure. Compound 11-dia1 is obtained according to the procedure described for compound 10, from 20-dia1 (550 mg, 1.23 mmol). Yellow oil (160 mg, 44%). The $^1$H/$^{13}$C NMR spectra and the mass spectrometry are in accordance with the expected structure.

Synthesis of Compounds 20-Dia2 and 11-Dia2

Compound 20-dia2 is obtained according to the procedure described for compound 19, from lactone L2-dia2 (1.5 g, 4.7 mmol), L-serine ethyl ester hydrochloride (804 mg, 4.7 mmol) and DIEA (4.1 ml, 24 mmol). Sticky white powder (860 mg). The $^1$H/$^{13}$C NMR spectra and the mass spectrometry are in accordance with the expected structure.

Compound 11-dia2 is obtained according to the procedure described for compound 10, from 20-dia2 (810 mg, 1.8 mmol). Yellow oil (380 mg, 72%, 2 steps). The $^1$H/$^{13}$C NMR spectra and the mass spectrometry are in accordance with the expected structure.

Synthesis of Compound 21

Compound 21 is obtained according to the procedure described for compound 19, from lactone L2 (1.07 g, 3.4 mmol), L-sarcosine ethyl ester (520 mg, 3.4 mmol) and DIEA (7.1 ml, 41 mmol). Hard orange wax. The $^1$H/$^{13}$C NMR spectra and the mass spectrometry are in accordance with the expected structure.

Example 2: Demonstration of the Depigmenting Activity

The measurement of the depigmenting activity (reduction of melanin production) of compounds of formula (I) was performed by assaying normal human melanocytes in vitro as follows.

First, normal human melanocytes are cultured and distributed in wells. After 24 hours, the culture medium was replaced with a medium containing the compounds of formula (I) to be evaluated. The cells were incubated for 72 hours before measuring the final optical density, which measures the amount of melanin produced by the melanocytes. The compounds are tested at 100 µM after calibration.

Various test runs were performed and the results are collated in the following table.

| Compound No. | % Depigmentation at 100 µM (run 1) | % depigmentation at 100 µM (run 2) |
| --- | --- | --- |
| 1 | 13% | |
| 4 | 19% | |
| 5 | 31% | |
| 6 | 29% | |
| 7 | 34% | |
| 10 | 20% | |
| 11-dia1 | 28% | |
| 11-dia2 | | 32% |
| 12 | | 20% (28% at the max dose tested 200 µM) |
| 19 | | 15% (43% at the max dose tested 200 µM) |
| 20-dia1 | | 23% |

The compounds of formula (I) showed a depigmenting effect.

Example 3: Cosmetic Composition

A skin depigmenting composition is prepared, comprising (in grams):

| | |
| --- | --- |
| Compound NO. 10 | 2 g |
| PEG400 | 68 g |
| Ethanol | 30 g |

The composition applied to the skin makes it possible to fade out brown spots.

A similar composition is prepared with compound I1 (trans- or cis isomers or a mixture of the two).

Example 5: Gel

A skin depigmenting composition is prepared, comprising (% by weight):

| | |
| --- | --- |
| Compound NO. 10 | 0.25% |
| Carbomer (carbopol 981 from Lubrizol) | 1% |
| Preserving agent | qs |
| Water | qs 100% |

The composition applied to the skin makes it possible to fade out brown spots.

A similar composition is prepared with compound 11 (trans or cis isomers or a mixture of the two).

Example 6

An anti-ageing gel for the skin is prepared, comprising (% by weight):

| | |
|---|---|
| compound 10 | 2% |
| Hydroxypropylcellulose (Klucel H from Hercules) | 1% |
| fragrance, preservative | qs |
| isopropanol | 40% |
| water | qs 100% |

A similar composition is prepared with compound 11 (trans or cis isomers or mixture of the two).

The invention claimed is:

1. A cosmetic non-therapeutic process for the depigmentation, lightening and/or bleaching of human skin, comprising the application of a compound of formula (I) or of a composition comprising one or more compounds of formula (I):

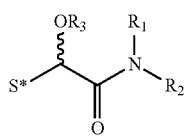
(I)

in which:
S* denotes a monosaccharide sugar radical chosen from glucose and xylose comprising one or more hydroxyl groups optionally substituted with a radical R' chosen from:
  i) $(C_1-C_6)$alkyl; or
  ii) $(C_2-C_6)$alkenyl; or
  iii) an acetyl radical; or
  iv) a protective group (PG) for hydroxyl function(s);
said monosaccharide radical optionally comprising one or more amino groups $NR_bR_c$ with $R_b$ and $R_c$, which may be identical or different, representing a hydrogen atom, an acetyl group, or a protective group for the amino function;
said monosaccharide radical being connected to the rest of the molecule by a bond between the $C_1$ carbon atom of one of the sugars of said monosaccharide radical, this bond possibly being α or β anomeric;
$R_3$ represents
  i) a hydrogen atom; or
  ii) a $(C_1-C_{18})$alkyl group; or
  iii) a $(C_2-C_{18})$alkenyl group; or
  iv) a hydroxyl-function-protective group (PG);
$R_1$ represents:
  i) a hydrogen atom; or
  ii) a $(C_1-C_{18})$alkyl group; or
  iii) a $(C_2-C_{18})$alkenyl group;
$R_2$ represents
i) an optionally substituted aryl or heteroaryl radical; or
(ii) a radical of formula (B1):

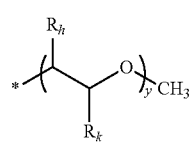
(B1)

in which:
$R_h$ and $R_k$, independently of one another, denote a hydrogen atom or a methyl radical, it being understood that $R_h$ and $R_k$ cannot simultaneously denote a methyl radical;
y=1 to 10; or iii) a radical of formula (B2):

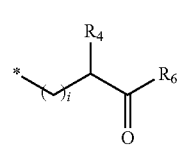
(B2)

in which:
i=0 or 1;
$R_4$ represents
  i) a hydrogen atom, or
  ii) a radical chosen from the radicals (a1) to (a32) described below:

(a1)

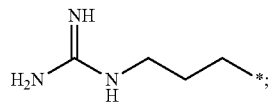
(a2)

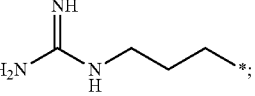
(a3)

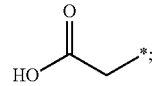
(a4)

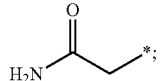
(a5)

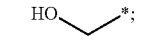
(a6)

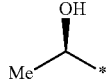
(a7)

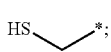
(a8)

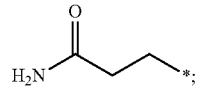
(a9)

(a10)

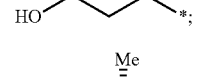
(a11)

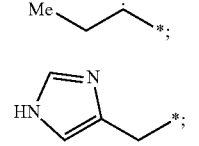
(a12)

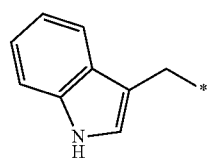

83
-continued

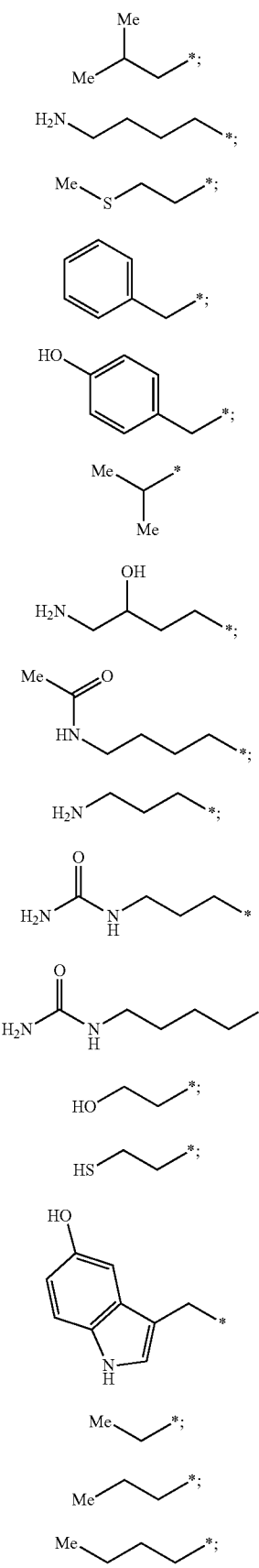

(a13)
(a14)
(a15)
(a16)
(a17)
(a18)
(a19)
(a20)
(a21)
(a22)
(a23)
(a24)
(a25)
(a26)
(a27)
(a28)
(a29)

84
-continued

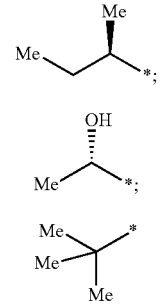

(a30)
(a31)
(a32)

or iii) R$_4$ can also form, with R$_1$ and the nitrogen atom which bears R$_1$, a saturated heterocycle of formula A1, or A2 or A3:

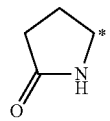

A1

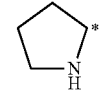

A2

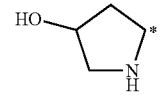

A3

R$_6$ denotes
   i) a hydroxyl radical OH; or
   ii) an alkoxide —O$^-$, M$^=$ with M$^=$ representing a cation; or
   iii) a saturated or unsaturated (C$_1$-C$_6$)alkoxy radical; or
   iv) a radical —NR$_f$R$_g$ with R$_f$ and R$_g$, which may be identical or different, representing a hydrogen atom or a (C$_1$-C$_6$)alkyl group.

2. The process according to claim 1, in which the compound(s) of formula (I) comprise(s) a radical R$_3$ which represents a hydrogen atom, R$_1$ which represents a hydrogen atom or a (C$_1$-C$_{18}$)alkyl group and R$_2$ which represents an aryl or heteroaryl radical, which is optionally substituted.

3. The process according to claim 1, in which the compound(s) of formula (I) comprise(s) a radical R$_2$ which represents a radical (B1) below:

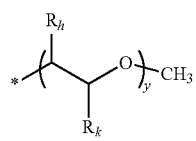

(B1)

in which:
   R$_h$ and R$_k$, independently of one another, denote a hydrogen atom or a methyl radical, it being understood that R$_h$ and R$_k$ cannot simultaneously denote a methyl radical;
   y =1 to 10.

4. The process according to claim 1, in which the compound(s) of formula (I) comprise(s) a radical $R_2$ which represents the radical (B2) below:
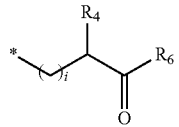
(B2)
in which:
  i=0 or 1;
  $R_4$ represents
   i) a hydrogen atom, or
   ii) is chosen from the radicals (a1) to (a32) described below:
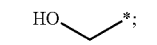 (a1)
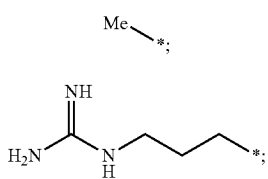 (a2)
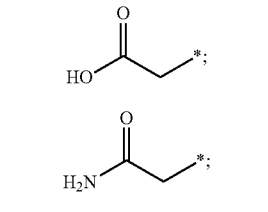 (a3)
(a4)
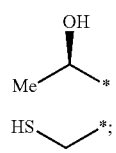 (a5)
(a6)
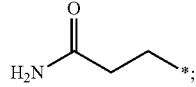 (a7)
(a8)
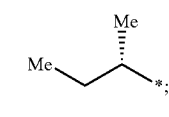 (a9)
(a10)
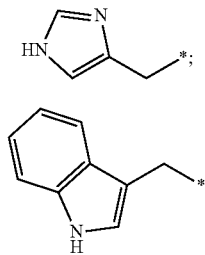 (a11)
(a12)
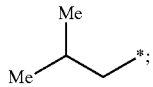 (a13)
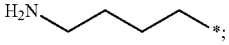 (a14)
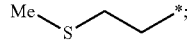 (a15)
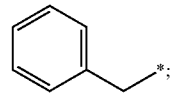 (a16)
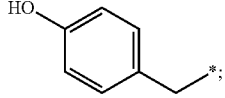 (a17)
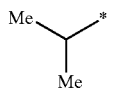 (a18)
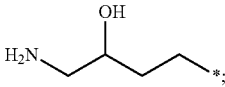 (a19)
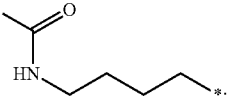 (a20)
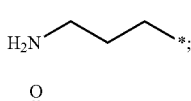 (a21)
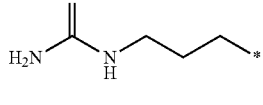 (a22)
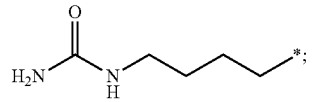 (a23)
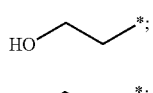 (a24)
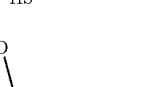 (a25)
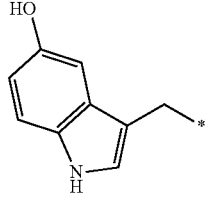 (a26)
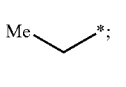 (a27)
(a28)
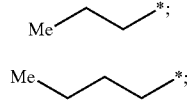 (a29)

(a30) 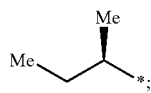

(a31) 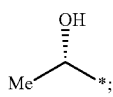

(a32) 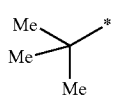

or iii) R₄ can also form, with R₁ and the nitrogen atom which bears R₁, a saturated heterocycle of formula A1, A2 or A3:

A1 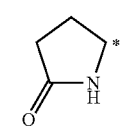

A2 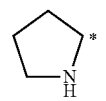

A3 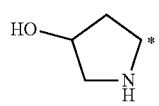

R₆ denotes
  i) a hydroxyl radical —OH; or
  ii) an alkoxide —O⁻, M⁺ with M⁺ representing a cation; or
  iii) a saturated or unsaturated ($C_1$-$C_6$)alkoxy radical; or
  iv) a radical —NR$_f$R$_g$ with R$_f$ and R$_g$, which may be identical or different, representing a hydrogen atom or a ($C_1$-$C_6$)alkyl group.

5. The process according to claim 1, in which the compound(s) of formula (I) is (are) chosen from the compounds of formulae (I') below:

(I') 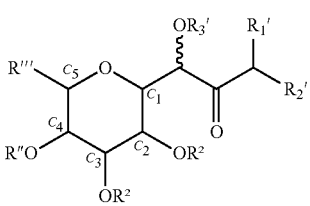

(I″) 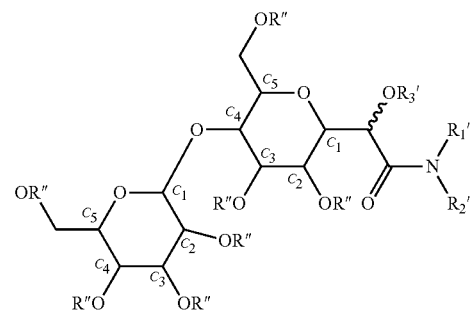

(I‴) 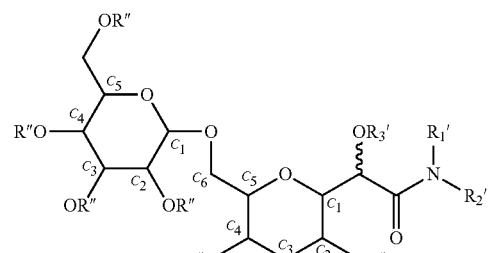

(I″a) 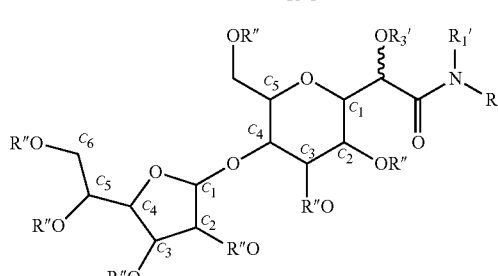

(I'a) 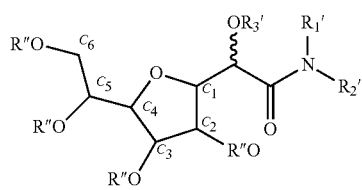

(I‴a) 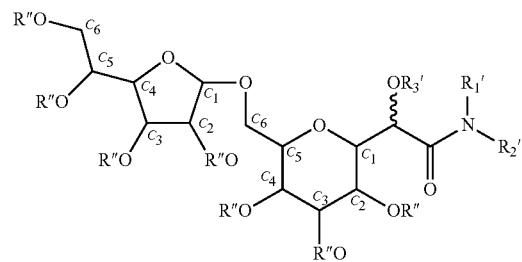

and also the solvates thereof, the optical and geometric isomers and tautomers thereof and the organic or mineral base or acid salts thereof in which formulae (I'):
  R₁' has the same definition as that of R₁ for the compounds of formula (I)
  R₂' has the same definition as that of R₂ for the compounds of formula (I)
  R₃' has the same definition as that of R₃ for the compounds of formula (I)

R" represents
i) ($C_1$-$C_6$)alkyl; or
ii) ($C_2$-$C_6$)alkenyl; or
iii) an acetyl radical; or
iv) a protective group (PG) for hydroxyl function(s); or
v) a hydrogen atom optionally substituted with a radical R' chosen from:
i) ($C_1$-$C_6$)alkyl; or
ii) ($C_2$-$C_6$)alkenyl; or
iii) an acetyl radical; or
iv) a protective group (PG) for hydroxyl function(s), R''' represents a hydrogen atom optionally substituted with a radical R' chosen from:
i) ($C_1$-$C_6$)alkyl; or
ii) ($C_2$-$C_6$)alkenyl; or
iii) an acetyl radical; or
iv) a protective group (PG) for hydroxyl function(s).

6. The process according to claim 1, in which the compound(s) of formula (I) is (are) chosen from the following compounds:

| S* | compound | structure |
| --- | --- | --- |
| D-glucose | 1 | |
| D-glucose | 2 | |
| D-glucose | 3 | |
| D-glucosee | 4 | 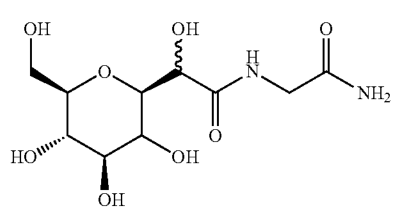 [SMILES: NC(=O)CNC(=O)C(O)[C@@H]1O[C@H](CO)[C@@H](O)[C@H](O)C1O] |
| D-glucose | 5 | |

-continued

| S* | compound | structure |
|---|---|---|
| D-glucose | 6 | |
| D-glucose | 7 | |
| D-glucose | 9 | |
| D-xylose | 10 | |
| D-xylose | 11-dia1 | |
| D-xylose | 11-dia2 | |
| D-xylose | 12 | |

-continued

| S* | compound | structure |
|---|---|---|
| D-xylose | 13 | 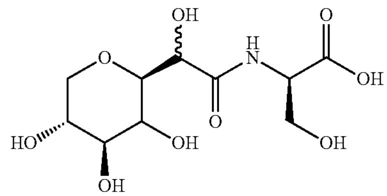 [SMILES: O=C(N[C@H](CO)C(=O)O)C(O)[C@@H]1OC[C@@H](O)[C@H](O)C1O] |
| D-glucose | 14 | |
| D-glucose | 15 | |
| D-glucose | 16 | |
| D-glucose | 17 | |

-continued
| S* | compound | structure |
|---|---|---|
| D-glucose | 18 | 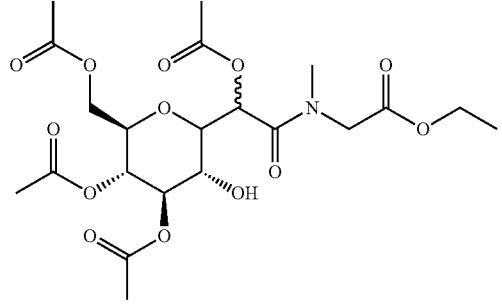 [SMILES: CCOC(=O)CN(C)C(=O)C(OC(C)=O)C1O[C@H](COC(C)=O)[C@@H](OC(C)=O)[C@H](OC(C)=O)[C@H]1O] |
| D-xylose | 19 | 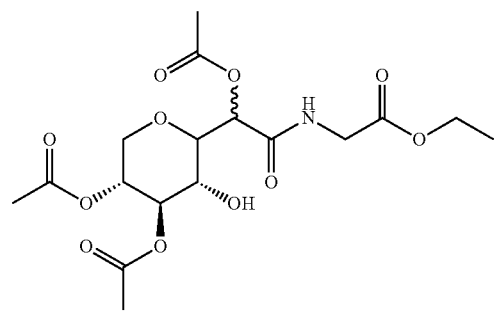 [SMILES: CCOC(=O)CNC(=O)C(OC(C)=O)C1OC[C@@H](OC(C)=O)[C@H](OC(C)=O)[C@H]1O] |
| D-xylose | 20-dia1 | 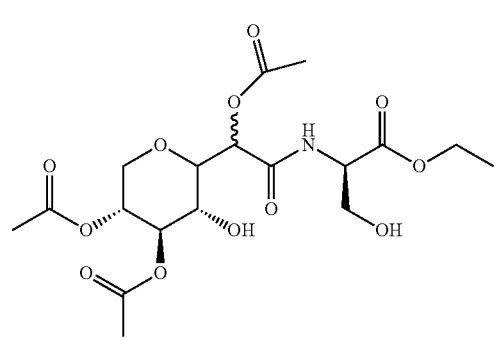 [SMILES: CCOC(=O)[C@@H](CO)NC(=O)C(OC(C)=O)C1OC[C@@H](OC(C)=O)[C@H](OC(C)=O)[C@H]1O] |
| D-xylose | 20-dia2 | 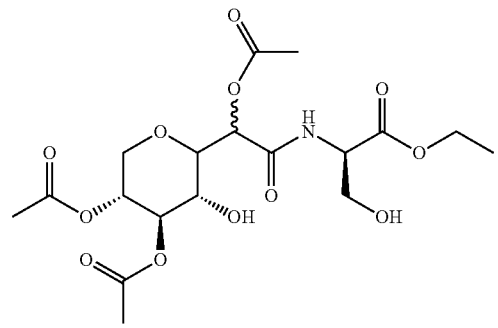 [SMILES: CCOC(=O)[C@@H](CO)NC(=O)C(OC(C)=O)C1OC[C@@H](OC(C)=O)[C@H](OC(C)=O)[C@H]1O] |

| S* | compound | structure |
|---|---|---|
| D-xylose | 21 | 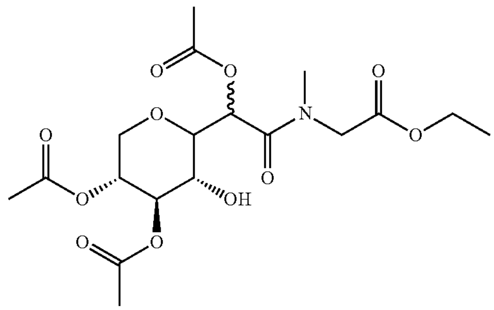 [SMILES: CCOC(=O)CN(C)C(=O)C(OC(C)=O)C1OC[C@@H](OC(C)=O)[C@H](OC(C)=O)[C@H]1O] |

7. The process according to claim 1, wherein S* denotes a sugar chosen from D-glucose and D-xylose.

8. The process according to claim 1, wherein $R_3$ represents a hydrogen atom or an acetyl group, $R_1$ represents a hydrogen radical, and $R_2$ represents an aryl radical optionally substituted with a phenyl radical substituted with one or more groups chosen from methoxy, hydroxyl, carboxy, acetyloxy and/or benzyloxycarbonyl.

9. The process according to claim 1, wherein S* denotes a monosaccharide sugar radical chosen D-glucose and D-xylose; $R_3$ represents a hydrogen atom; $R_1$ represents a hydrogen atom or methyl; and $R_2$ denotes a radical of formula (B2):

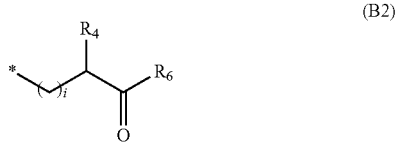 (B2)

in which
i=0 or 1,
$R_6$ represents an ethoxy, hydroxyl or $NH_2$ radical, $R_4$ represents a hydrogen atom, and when i=0, $R_4$ represents a hydroxymethyl radical of formula (a5)

$$HO\frown*\qquad(a5)$$

or else $R_4$ can form, with $R_1$ and the nitrogen atom which bears $R_1$, a saturated heterocycle of formula A2:

 A2

10. The process according to claim 9, wherein S* denotes a monosaccharide sugar radical chosen from glucose and xylose, having C3, and C4 and where appropriate C6 hydroxyl groups substituted with an acetyl group.

* * * * *